United States Patent
Klar et al.

(10) Patent No.: US 9,034,856 B2
(45) Date of Patent: May 19, 2015

(54) 17-(1'PROPENYL)-17-3'-OXIDOESTRA-4-EN-3-ONE DERIVATIVE, USE THEREOF, AND MEDICAMENT CONTAINING SAID DERIVATIVE

(75) Inventors: Ulrich Klar, Berlin (DE); Joachim Kuhnke, Potsdam (DE); Rolf Bohlmann, Berlin (DE); Jan Hübner, Berlin (DE); Sven Ring, Jena (DE); Thomas Frenzel, Hofheim (DE); Frederik Menges, Schriesheim (DE); Steffen Borden, Berlin (DE); Hans Peter Muhn, Berlin (DE); Katja Prelle, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 381 days.

(21) Appl. No.: 12/810,858

(22) PCT Filed: Dec. 23, 2008

(86) PCT No.: PCT/EP2008/011161
§ 371 (c)(1),
(2), (4) Date: Aug. 31, 2010

(87) PCT Pub. No.: WO2009/083268
PCT Pub. Date: Jul. 9, 2009

(65) Prior Publication Data
US 2010/0317632 A1  Dec. 16, 2010

(30) Foreign Application Priority Data
Dec. 29, 2007  (DE) .......................... 10 2007 063 500

(51) Int. Cl.
| | | |
|---|---|---|
| *A61K 31/58* | (2006.01) | |
| *C07J 21/00* | (2006.01) | |
| *C07J 41/00* | (2006.01) | |
| *C07J 53/00* | (2006.01) | |

(52) U.S. Cl.
CPC .............. *C07J 21/00* (2013.01); *C07J 41/0016* (2013.01); *C07J 53/001* (2013.01); *C07J 53/007* (2013.01)

(58) Field of Classification Search
CPC ...... C07J 21/00; C07J 41/0016; C07J 53/001; C07J 53/007; A61K 31/58
USPC ............................................ 540/28; 514/173
See application file for complete search history.

(56) References Cited

U.S. PATENT DOCUMENTS

| | | | |
|---|---|---|---|
| 3,757,009 | A | 9/1973 | Georg Anner |
| 3,764,596 | A | 10/1973 | Galantay |
| 4,870,069 | A | 9/1989 | Ottow et al. |
| 4,912,097 | A | 3/1990 | Teutsch et al. |

FOREIGN PATENT DOCUMENTS

| | | |
|---|---|---|
| EP | 0 245 170 A1 | 11/1987 |
| EP | 0 277 089 A1 | 8/1988 |
| WO | 94/06819 A1 | 3/1994 |
| WO | 2006/072467 A1 | 7/2006 |

OTHER PUBLICATIONS

International Search Report of PCT/EP2008/011161 (Jun. 8, 2009).
T. N. Mellin et al., "Chemical Inhibition of Estrus in the Beagle", Theriogenology, vol. 5, No. 4 (1976) pp. 165-174.
J. R. Brooks et al., "Biological Spectrum of Two Spirolactone Derivatives with some Observations on Anti-Fertility Activity", Steroids, Elsevier Science Publishers, vol. 29, No. 6 (Jun. 1, 1977) pp. 809-821.
Klaus Nickisch, Sybille Beier, Dieter Bittler, Walter Iclger, Henry Laurent, Wolfgang Losert, Yukishige Nishino, Ekkehard Schillinger, and Rudolf Wiechert, "Aldosterone Antagonists. 4. Synthesis and Activities of Steroidal 6,6-Ethylene-15,16-methylene 17-Spirolactones," J. Med. Chem., vol. 34, No. 8, pp. 2464-2468 (Aug. 1, 1991).

*Primary Examiner* — Barbara P Badio
(74) *Attorney, Agent, or Firm* — Karen B. King; Thomas C. Blankinship

(57) ABSTRACT

The invention relates to 17-(1'-propenyl)-17-3'-oxidoestra-4-en-3-one derivatives with the general chemical formula I, where the residues Z, $R^4$, $R^{6a}$, $R^{6b}$, $R^7$, $R^{15}$, $R^{16a}$, $R^{16b}$ and $R^{18}$ have the meanings stated in Claim 1, and their solvates, hydrates and salts, including all stereoisomers of these compounds. The invention further relates to the use of these derivatives for the production of a medicinal product for oral contraception and for the treatment of pre-, peri- and post-menopausal complaints and medicinal products that contain said derivatives, and in particular application in the aforementioned indications. The derivatives according to the invention have a progestational and in preferred cases additionally an antimineralocorticoid and neutral to slightly androgenic action.

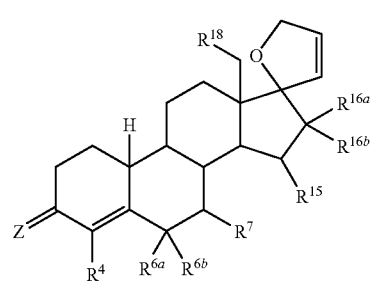

I

9 Claims, No Drawings

17-(1'PROPENYL)-17-3'-OXIDOESTRA-4-EN-3-ONE DERIVATIVE, USE THEREOF, AND MEDICAMENT CONTAINING SAID DERIVATIVE

The invention relates to 17-(1'-propenyl)-17-3'-oxidoestra-4-en-3-one derivatives with progestational action, use thereof and medicinal products containing the derivatives, for example for the treatment of pre-, peri- and postmenopausal and premenstrual complaints.

Compounds with progestational, antimineralocorticoid, antiandrogenic or antiestrogenic action based on a steroid structure are known from the literature, derived for example from 19-nor-androst-4-en-3-one or a derivative thereof (the numbering of the steroid structure is given for example in Fresenius/Görlitzer 3rd Ed. 1991 "Organic-Chemical Nomenclature" p. 60 ff.).

Thus, WO 2006/072467 A1 discloses the compound 6β,7β-15β,16β-dimethylene-3-oxo-17-pregn-4-ene-21,17β-carbolactone(drospirenone), which has progestational action and has been used for example in an oral contraceptive and in a preparation for the treatment of postmenopausal complaints. Owing to its comparatively low affinity for the progestogen receptor and its comparatively high ovulation-inhibiting dose, however, drospirenone is contained in the contraceptive at the relatively high daily dose of 3 mg. Drospirenone is, moreover, also characterized in that in addition to the progestational action it also has aldosterone-antagonistic (antimineralocorticoid) and antiandrogenic action. These two properties make drospirenone very similar in its pharmacological profile to the natural progestogen, progesterone, which however, unlike drospirenone, is not sufficiently bioavailable orally. In order to lower the dose to be administered, WO 2006/072467 A1 further proposes an 18-methyl-19-nor-17-pregn-4-ene-21,17-carbolactone and pharmaceutical preparations containing this, which have a higher progestational potency than drospirenone.

In addition, U.S. Pat. No. 3,705,179, for example, discloses steroids that display antiandrogenic activity and are suitable for the treatment of diseases that are linked to androgens.

Moreover, EP 0 245 170 A1 discloses steroid compounds containing an unsaturated spiroether in position 17 and an aromatic residue in position 11. The action of these compounds is stated to be progestomimetic or antiprogestomimetic, androgenic or antiandrogenic and antiglucocorticoid.

The aim of the present invention is to make compounds available that bind strongly to the progestogen receptor. Moreover, the compounds should preferably also have antimineralocorticoid action and, with respect to the androgen receptor, a neutral to slightly androgenic action. Another essential aim of the present invention consists of achieving a balanced action profile with respect to the progestational action to the antimineralocorticoid action, so that the ratio of the progestational action to the antimineralocorticoid action is less than with drospirenone.

This aim is achieved with the 17-(1'-propenyl)-17-3'-oxidoestra-4-en-3-one derivatives of the present invention, the use of the derivatives according to the invention, and a medicinal product containing at least one derivative according to the invention, in particular for oral contraception and for the treatment of pre-, peri- and postmenopausal complaints. Advantageous embodiments of the invention are stated herein.

The numbering of the carbon backbone of the derivatives according to the invention with the general chemical formula I follows the numbering of a steroid structure in the usual way, as described for example in Fresenius, loc. cit. The numbering of the residues stated in the claims corresponds in a similar manner to their bonding position on the carbon backbone of the derivatives, as far as this relates to $R^4$, $R^6$, $R^7$, $R^{15}$, $R^{16}$ and $R^{18}$. For example, the residue $R^4$ binds to the $C^4$-position of the derivative according to the invention.

With respect to the groups defined for Z, the groups NOR' and $NNHSO_2R'$ each bind with a double bond via N to the carbon backbone of the derivative according to =NOR' or =NNH—$SO_2R'$. OR' in NOR' and $NHSO_2R'$ in $NNHSO_2R'$ can be in syn- or anti-position.

Alkyl in R', $R^{6a}$, $R^{6b}$, $R^7$, $R^{16a}$, $R^{16b}$, $R^{18}$, $R^{19}$, $R^{20}$, $R^{21a}$, $R^{21b}$ and $R^{22}$ and in other cases means linear or branched alkyl groups with the stated number of carbon atoms or optionally with 1-10 carbon atoms, for example methyl, ethyl, propyl, isopropyl, butyl, isobutyl, tent.-butyl, pentyl, isopentyl, neopentyl, hexyl, heptyl, decyl. Alkyl in $R^{18}$ means in particular methyl, ethyl, propyl or isopropyl and $R^{22}$ means methyl, ethyl, propyl, isopropyl, butyl, isobutyl, tert-butyl, pentyl, isopentyl, neopentyl, hexyl. The alkyl groups R', $R^{6a}$, $R^{6b}$, $R^7$, $R^{16a}$, $R^{16b}$, $R^{18}$, $R^{19}$, $R^{20}$, $R^{21a}$, $R^{21b}$ and $R^{22}$ can moreover be perfluorinated or can be substituted with 1-5 halogen atoms, hydroxyl groups, $C_1$-$C_4$-alkoxy groups, $C_6$-$C_{12}$-aryl groups (which in their turn can be substituted with 1-3 halogen atoms). In particular, alkyl can therefore also stand for hydroxymethylene (HO—$CH_2$), hydroxyethylene (HO—$C_2H_4$), hydroxypropylene (HO—$C_3H_6$) and hydroxybutylene (HO—$C_4H_8$) and their isomers.

Alkenyl in $R^{6a}$, $R^{6b}$ and $R^7$ means linear or branched alkenyl groups with 2-10 carbon atoms, for example vinyl, propenyl, butenyl, pentenyl, isobutenyl, isopentenyl.

Alkynyl in $R^{6a}$, $R^{6b}$ and $R^7$ means linear or branched alkynyl groups with 2-10 carbon atoms, for example ethynyl, propynyl, butynyl, pentynyl, isobutynyl, isopentynyl.

The alkenyl and alkynyl groups $R^{6a}$, $R^{6a}$ and $R^7$ can be substituted with 1-5 halogen atoms, hydroxyl groups, $C_1$-$C_3$-alkoxy groups, $C_6$-$C_{12}$-aryl groups (which in their turn can be substituted with 1-3 halogen atoms).

Cycloalkyl in $R^7$ means cycloalkyl groups with 3-6 carbon atoms, for example cyclopropyl, cyclobutyl, cyclopentyl and cyclohexyl. The cycloalkyl groups $R^7$ can be substituted with halogen, OH, O-alkyl, $CO_2H$, $CO_2$-alkyl, $NH_2$, $NO_2$, $N_3$, CN, $C_1$-$C_{10}$-alkyl, $C_1$-$C_{10}$-acyl, $C_1$-$C_{10}$-acyloxy groups.

Aryl in R' and in other cases means substituted and unsubstituted carbocyclic or heterocyclic residues with one or more heteroatoms, e.g. phenyl, naphthyl, furyl, thienyl, pyridyl, pyrazolyl, pyrimidinyl, oxazolyl, pyridazinyl, pyrazinyl, quinolyl, thiazolyl, which can be substituted singly or multiply with halogen, OH, O-alkyl, $CO_2H$, $CO_2$-alkyl, $NH_2$, $NO_2$, $N_3$, CN, $C_1$-$C_{10}$-alkyl, $C_1$-$C_{10}$-acyl, $C_1$-$C_{10}$-acyloxy groups. If aryl is otherwise mentioned as substituent on alkyl, alkenyl or alkynyl, this refers in particular to aryl groups with 6-12 ring carbon atoms.

Aralkyl in R' means aralkyl groups that can contain up to 14 carbon atoms, preferably 6 to 10 carbon atoms, in the ring, and 1 to 8, preferably 1 to 4, carbon atoms in the alkyl chain. As aralkyl residues, consideration can be given for example to benzyl, phenylethyl, naphthylmethyl, naphthylethyl, furylmethyl, thienylethyl, pyridylpropyl. The rings can be substituted singly or multiply with halogen, OH, O-alkyl, $CO_2H$, $CO_2$-alkyl, $NO_2$, $N_3$, CN, $C_1$-$C_{20}$-alkyl, $C_1$-$C_{20}$-acyl, $C_1$-$C_{20}$-acyloxy groups.

If alkoxy (O-alkyl) is mentioned, this refers to alkoxy groups with 1-4 carbon atoms. Alkoxy can in particular be methoxy, ethoxy and propoxy.

If acyl (CO-alkyl) is mentioned, this refers to acyl groups with 1-20 carbon atoms. Acyl can in particular be formyl, acetyl, propionyl and butyryl.

If acyloxy (O—CO-alkyl) is mentioned, this refers to acyloxy groups with 1-20 carbon atoms. Acyloxy can in particular be formyloxy, acetyloxy, propionyloxy and butyryloxy.

Halogen means fluorine, chlorine or bromine. Of these, chlorine is preferred.

The present invention relates to 17-(1'-propenyl)-17-3'-oxidoestra-4-en-3-one derivatives with the general chemical formula I:

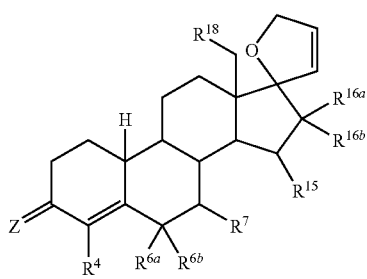

in which
Z is selected from the group comprising oxygen, two hydrogen atoms, NOR' and NNHSO$_2$R', where R' is hydrogen, $C_1$-$C_{10}$-alkyl, aryl or $C_7$-$C_{20}$-aralkyl,
$R^4$ is selected from the group comprising hydrogen and halogen,
furthermore either:
$R^{6a}$, $R^{6b}$ each independently of one another are selected from the group comprising hydrogen, $C_1$-$C_{10}$-alkyl, $C_2$-$C_{10}$-alkenyl and $C_2$-$C_{10}$-alkynyl or together form methylene or 1,2-ethanediyl and
$R^7$ is selected from the group comprising hydrogen, $C_1$-$C_{10}$-alkyl, $C_3$-$C_6$-cycloalkyl, $C_2$-$C_{10}$-alkenyl and $C_2$-$C_{10}$-alkynyl,
or:
$R^{6a}$, $R^7$ together form oxygen or a methylene group or drop out with formation of a double bond between $C^6$ and $C^7$ and
$R^{6b}$ is selected from the group comprising hydrogen, $C_1$-$C_{10}$-alkyl, $C_2$-$C_{10}$-alkenyl and $C_2$-$C_{10}$-alkynyl,
furthermore either:
$R^{15}$ is hydrogen and
$R^{16a}$, $R^{16b}$ together form methylene or 1,2-ethanediyl or, each independently of one another, are selected from the group comprising hydrogen and $C_1$-$C_{10}$-alkyl,
or:
$R^{15}$, $R^{16a}$ together form oxygen or drop out with formation of a double bond between $C^{16}$ and $C^{16}$ and
$R^{16b}$ is selected from the group comprising hydrogen and $C_1$-$C_{10}$-alkyl and
$R^{18}$ is selected from the group comprising hydrogen and $C_1$-$C_3$-alkyl.

Furthermore, the invention also relates to the solvates, hydrates, and salts of the derivatives according to the invention, including all stereoisomers of these derivatives.

According to a preferred embodiment of the invention, Z is selected from the group comprising oxygen, NOR' and NNHSO$_2$R'.

According to another preferred embodiment of the invention, Z stands for oxygen.

According to another preferred embodiment of the invention, $R^4$ is selected from the group comprising hydrogen and chlorine.

According to another preferred embodiment of the invention, $R^{6a}$ and $R^{6b}$ together form 1,2-ethanediyl or are each hydrogen.

According to another preferred embodiment of the invention, $R^7$ is selected from the group comprising hydrogen, methyl, ethyl and vinyl.

According to another preferred embodiment of the invention, $R^{6a}$ and $R^7$ together form a methylene group.

According to another preferred embodiment of the invention, $R^{6a}$ and $R^7$ drop out with formation of a double bond between $C^6$ and $C^7$.

According to another preferred embodiment of the invention, $R^{15}$ is hydrogen.

According to another preferred embodiment of the invention, $R^{15}$ and $R^{16a}$ together form an oxygen atom or drop out with formation of a double bond between $C^{15}$ and $C^{16}$.

According to another preferred embodiment of the invention, $R^{16a}$ is hydrogen and $R^{16b}$ is methyl.

According to another preferred embodiment of the invention, $R^{16a}$ and $R^{16b}$ are hydrogen.

According to another preferred embodiment of the invention, $R^{16a}$ and $R^{16b}$ together form methylene.

According to another preferred embodiment of the invention, $R^{16a}$ and $R^{16b}$ together form 1,2-ethanediyl.

According to another preferred embodiment of the invention, $R^{18}$ is selected from the group comprising hydrogen and methyl.

Compounds with the general chemical formula I are especially preferred, in, which
Z is oxygen or NOR', where R' is hydrogen, $C_1$-$C_6$-alkyl, aryl or $C_7$-$C_{12}$-aralkyl,
$R^4$ is hydrogen or halogen,
furthermore either:
$R^{6a}$, $R^{6b}$ each independently of one another are selected from the group comprising hydrogen, $C_1$-$C_6$-alkyl, $C_2$-$C_6$-alkenyl, $C_2$-$C_6$-alkynyl, or together form methylene or 1,2-ethanediyl and
$R^7$ is hydrogen, $C_1$-$C_6$-alkyl, $C_3$-$C_6$-cycloalkyl, $C_2$-$C_6$-alkenyl or $C_2$-$C_6$-alkynyl,
or:
$R^{6a}$, $R^7$ together form a methylene group or drop out with formation of a double bond between $C^6$ and $C^7$ and
$R^{6b}$ is hydrogen, $C_1$-$C_6$-alkyl, $C_2$-$C_6$-alkenyl or $C_2$-$C_6$-alkynyl
furthermore either:
$R^{15}$ is hydrogen and
$R^{16a}$, $R^{16b}$ together form methylene or 1,2-ethanediyl or, each independently of one another, are selected from the group comprising hydrogen and $C_1$-$C_6$-alkyl, or
or:
$R^{15}$, $R^{16a}$ drop out with formation of a double bond between $C^{15}$ and $C^{16}$ and
$R^{16b}$ is selected from the group comprising hydrogen and $C_1$-$C_6$-alkyl, and
$R^{16}$ is hydrogen or $C_1$-$C_2$-alkyl,
also including in this case the solvates, hydrates and salts of the derivatives according to the invention, including all stereoisomers of these derivatives.

Compounds with the general chemical formula I are more especially preferred, in which
Z is oxygen or NOR', and R' is hydrogen or $C_1$-$C_3$-alkyl,
$R^4$ is hydrogen, chlorine or bromine,
furthermore either:
$R^{6a}$, $R^{6b}$ each independently of one another are selected from the group comprising hydrogen, $C_1$-$C_3$-alkyl and $C_2$-$C_4$-alkenyl, or together form methylene or 1,2-ethanediyl and $R^7$ is hydrogen, $C_1$-$C_4$-alkyl, $C_3$-$C_4$-cycloalkyl or $C_2$-$C_4$-alkenyl,
or:
$R^{6a}$, $R^7$ together form a methylene group or drop out with formation of a double bond between $C^6$ and $C^7$ and
$R^{6b}$ is hydrogen, $C_1$-$C_3$-alkyl or $C_2$-$C_4$-alkenyl and
furthermore either:
$R^{15}$ is hydrogen and
$R^{16a}$, $R^{16b}$ are hydrogen or together form methylene or 1,2-ethanediyl
or:
$R^{16a}$ drop out with formation of a double bond between $C^{15}$ and $C^{16}$ and
$R^{16b}$ is hydrogen and
$R^{18}$ is hydrogen or methyl,
also including in this case the solvates, hydrates and salts of the derivatives according to the invention, including all stereoisomers of these derivatives.

All possible stereoisomers and isomeric mixtures, including racemates, of the compounds with the general chemical formula I are hereby expressly included. Each of the stated substituents on the steroid basic structure can be both in an α position and in a β position. Furthermore, the substituents on the steroid basic structure that contain a double bond and in which the double bond on each carbon atom carries at least one substituent, which is not hydrogen, can be both E- and Z-configured. Groups bound to two adjacent carbon atoms of the structure, for example an oxygen atom, methylene or 1,2-ethanediyl, are bound either in α,α-position or in β,β-position.

Derivatives according to the invention in the form of solvates, in particular hydrates, are also expressly included, and the compounds according to the invention can accordingly contain polar solvents, in particular water, as structural element of the crystal lattice of the compounds according to the invention. The polar solvent, in particular water, can be present in stoichiometric proportions or even in nonstoichiometric proportions. Stoichiometric solvates and hydrates are also called hemi-, (semi-), mono-, sesqui-, di-, tri-, tetra-, penta-, etc. solvates or hydrates.

If an acid function is present, the physiologically compatible salts of organic and inorganic bases are suitable as salts, for example the readily soluble alkali-metal and alkaline-earth salts, and the salts of N-methyl-glucamine, D-methyl-glucamine, ethyl-glucamine, lysine, 1,6-hexadiamine, ethanolamine, glucosamine, sarcosine, serinol, Tris-hydroxy-methyl-aminomethane, aminopropanediol, Sovak base, 1-amino-2,3,4-butanetriol. If a basic function is present, the physiologically compatible salts of organic and inorganic acids are suitable, such as those of hydrochloric acid, sulfuric acid, phosphoric acid, citric acid, tartaric acid inter alia.

It was found that the compounds or derivatives according to the invention have good progestational action. Furthermore, some interesting compounds according to the invention interact with the mineralocorticoid receptor and are able to impart an antagonistic action. Moreover, the compounds according to the invention have a neutral to slightly androgenic action with respect to the androgen receptor. Another property of the majority of the compounds is that the bonds of these compounds to the progesterone receptor and to the mineralocorticoid receptor are balanced relative to one another, namely so that their ratio of the capacity for binding to the progesterone receptor to the capacity for binding to the mineralocorticoid receptor is less than in the case of drospirenone. Therefore the antimineralocorticoid action of these compounds at a given progestational action is less than with drospirenone. If the dosage of a given compound according to the invention is based on its progestational action, the antimineralocorticoid action of this compound at this dosage is therefore less than with drospirenone.

The compounds listed below are especially preferred (in addition, reference is also made to the examples of synthesis described later):

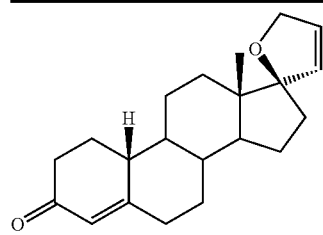

17α-(1'-Propenyl)-17β-3'-oxidoestra-4-en-3-one (Example 1)

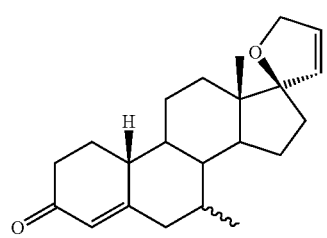

7α-Methyl-17α-(1'-propenyl)-17β-3'-oxidoestra-4-en-3-one (Example 3)
7β-Methyl-17α-(1'-propenyl)-17β-3'-oxidoestra-4-en-3-one

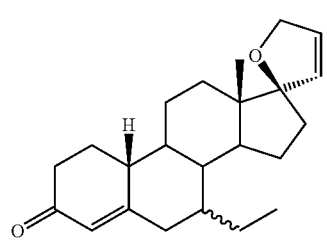

7α-Ethyl-17α-(1'-propenyl)-17β-3'-oxidoestra-4-en-3-one (Example 4)
7β-Ethyl-17α-(1'-propenyl)-17β-3'-oxidoestra-4-en-3-one (Example 4)

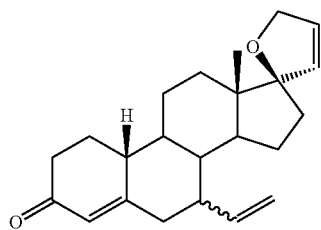 7α-Vinyl-17α-(1'-propenyl)-17β-3'-oxicloestra-4-en-3-one (Example 5)
7β-Vinyl-17α-(1'-propenyl)-17β-3'-oxidoestra-4-en-3-one

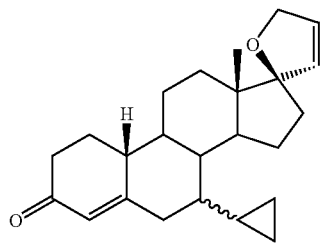 7α-Cyclopropyl-17α-(1'-propenyl)-17β-3'-oxidoestra-4-en-3-one (Example 15)
7β-Cyclopropyl-17α-(1'-propenyl)-17β-3'-oxidoestra-4-en-3-one

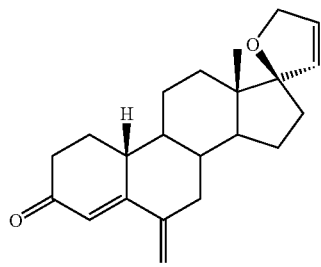 6-Methylene-17α-(1'-propenyl)-17β-3'-oxidoestra-4-en-3-one

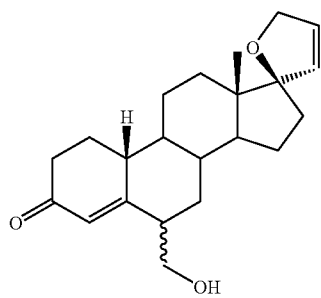 6α-Hydroxymethylene-17α-(1'-propenyl)-17β-3'-oxidoestra-4-en-3-one
6β-Hydroxymethylene-17α-(1'-propenyl)-17β-3'-oxidoestra-4-en-3-one

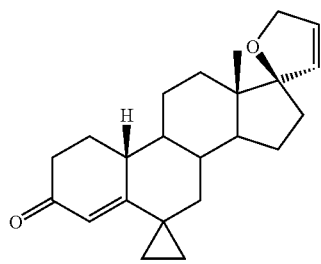 6,6-(1,2-Ethanediyl)-17α-(1'-propenyl)-17β-3'-oxidoestra-4-en-3-one (Example 16)

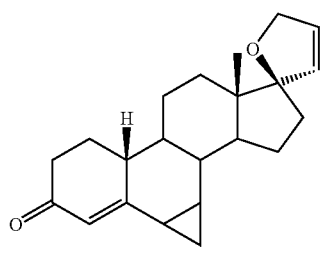 6α,7α-Methylene-17α-(1'-propenyl)-17β-3'-oxidoestra-4-en-3-one (Example 14B)
6β,7β-Methylene-17α-(1'-propenyl)-17β-3'-oxidoestra-4-en-3-one (Example 14A)

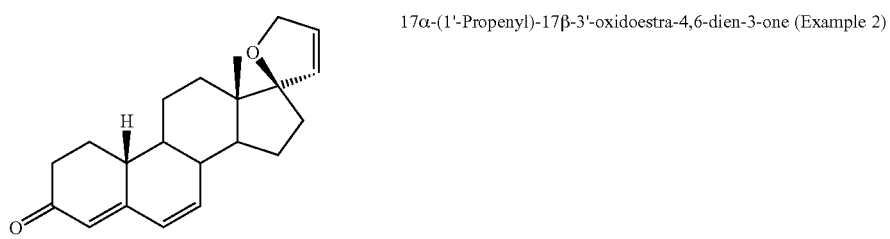

17α-(1'-Propenyl)-17β-3'-oxidoestra-4,6-dien-3-one (Example 2)

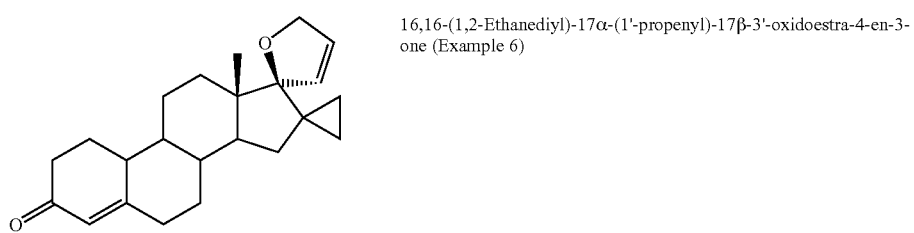

16,16-(1,2-Ethanediyl)-17α-(1'-propenyl)-17β-3'-oxidoestra-4-en-3-one (Example 6)

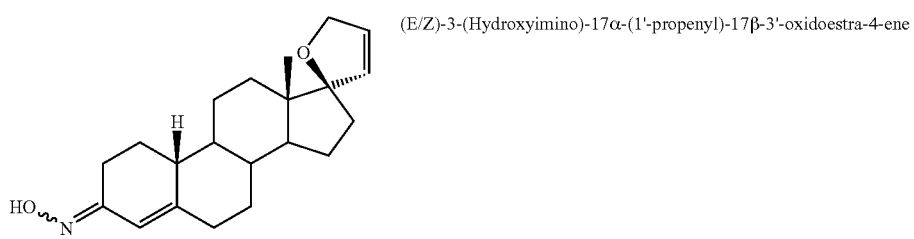

(E/Z)-3-(Hydroxyimino)-17α-(1'-propenyl)-17β-3'-oxidoestra-4-ene

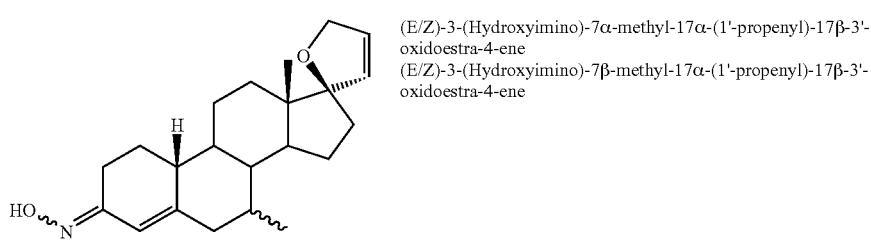

(E/Z)-3-(Hydroxyimino)-7α-methyl-17α-(1'-propenyl)-17β-3'-oxidoestra-4-ene
(E/Z)-3-(Hydroxyimino)-7β-methyl-17α-(1'-propenyl)-17β-3'-oxidoestra-4-ene

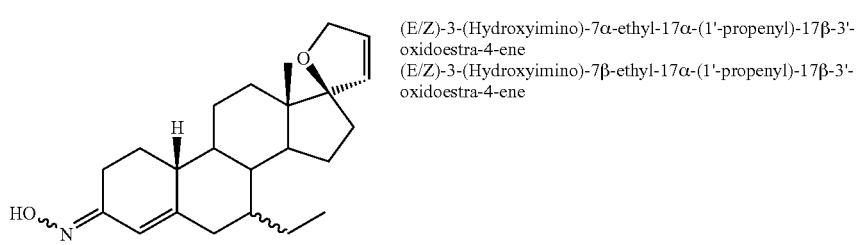

(E/Z)-3-(Hydroxyimino)-7α-ethyl-17α-(1'-propenyl)-17β-3'-oxidoestra-4-ene
(E/Z)-3-(Hydroxyimino)-7β-ethyl-17α-(1'-propenyl)-17β-3'-oxidoestra-4-ene

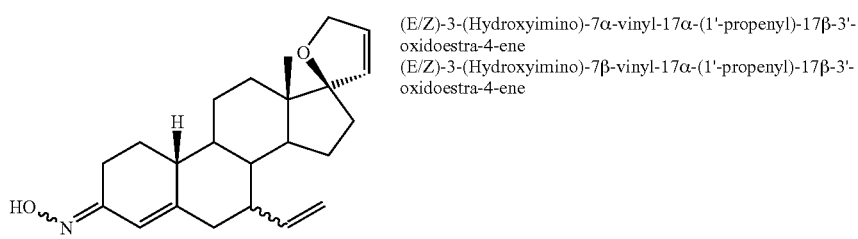

(E/Z)-3-(Hydroxyimino)-7α-vinyl-17α-(1'-propenyl)-17β-3'-oxidoestra-4-ene
(E/Z)-3-(Hydroxyimino)-7β-vinyl-17α-(1'-propenyl)-17β-3'-oxidoestra-4-ene

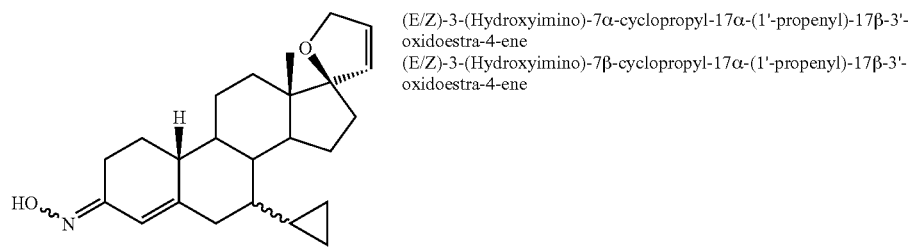
(E/Z)-3-(Hydroxyimino)-7α-cyclopropyl-17α-(1'-propenyl)-17β-3'-oxidoestra-4-ene
(E/Z)-3-(Hydroxyimino)-7β-cyclopropyl-17α-(1'-propenyl)-17β-3'-oxidoestra-4-ene

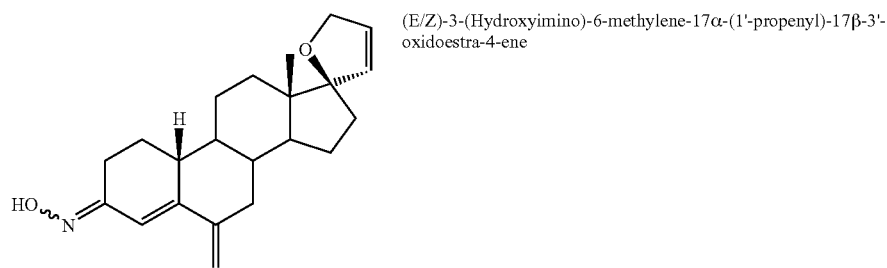
(E/Z)-3-(Hydroxyimino)-6-methylene-17α-(1'-propenyl)-17β-3'-oxidoestra-4-ene

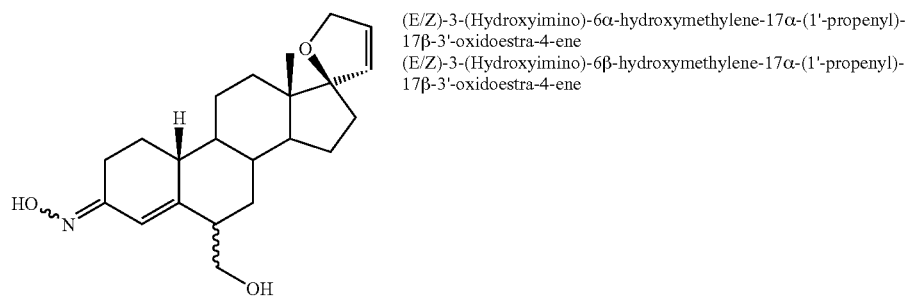
(E/Z)-3-(Hydroxyimino)-6α-hydroxymethylene-17α-(1'-propenyl)-17β-3'-oxidoestra-4-ene
(E/Z)-3-(Hydroxyimino)-6β-hydroxymethylene-17α-(1'-propenyl)-17β-3'-oxidoestra-4-ene

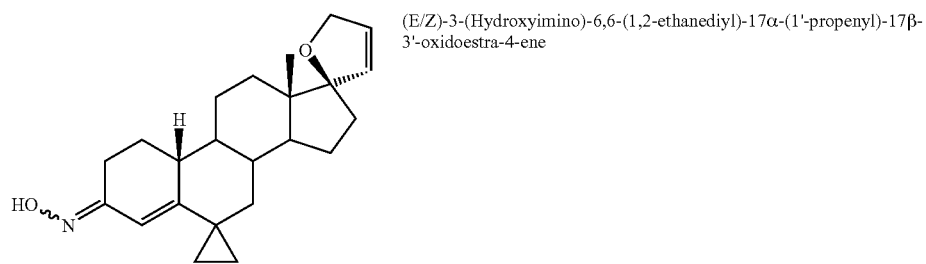
(E/Z)-3-(Hydroxyimino)-6,6-(1,2-ethanediyl)-17α-(1'-propenyl)-17β-3'-oxidoestra-4-ene

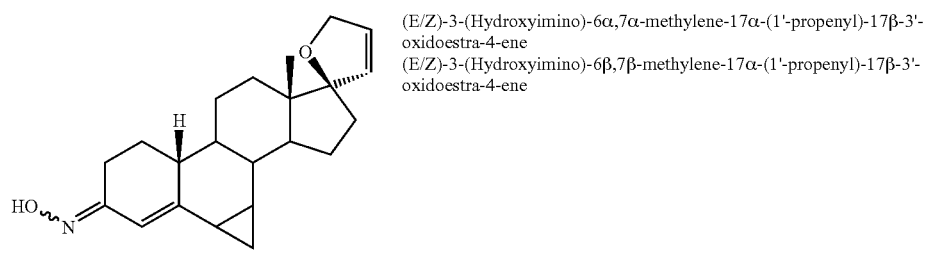
(E/Z)-3-(Hydroxyimino)-6α,7α-methylene-17α-(1'-propenyl)-17β-3'-oxidoestra-4-ene
(E/Z)-3-(Hydroxyimino)-6β,7β-methylene-17α-(1'-propenyl)-17β-3'-oxidoestra-4-ene

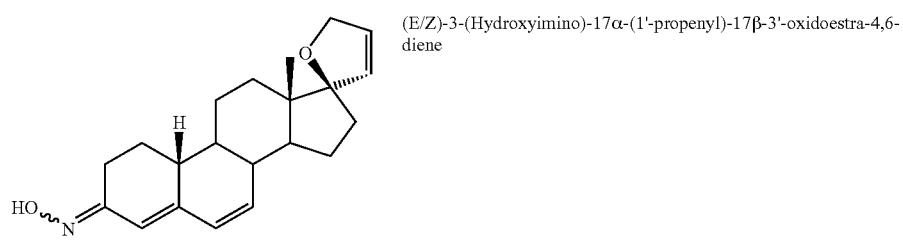
(E/Z)-3-(Hydroxyimino)-17α-(1'-propenyl)-17β-3'-oxidoestra-4,6-diene

-continued

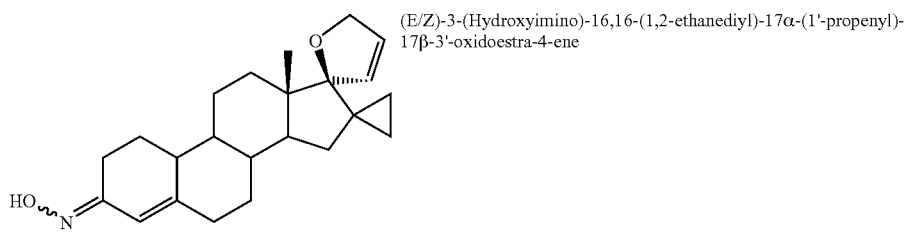

(E/Z)-3-(Hydroxyimino)-16,16-(1,2-ethanediyl)-17α-(1'-propenyl)-17β-3'-oxidoestra-4-ene

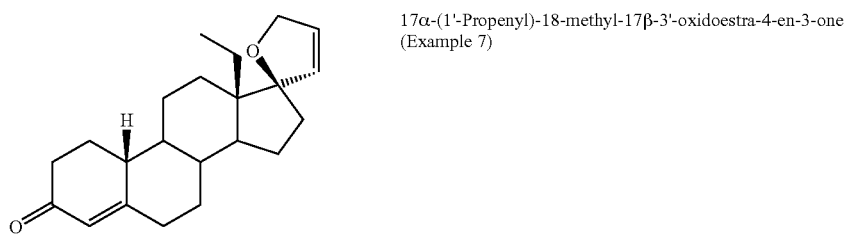

17α-(1'-Propenyl)-18-methyl-17β-3'-oxidoestra-4-en-3-one
(Example 7)

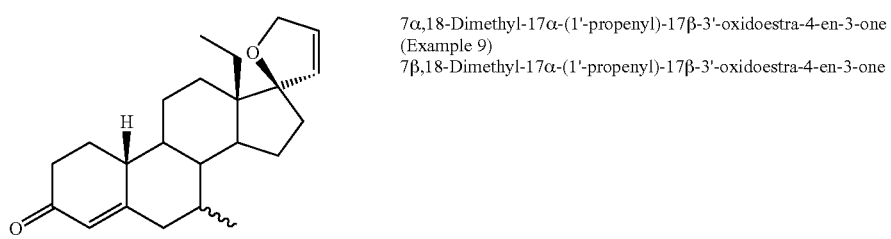

7α,18-Dimethyl-17α-(1'-propenyl)-17β-3'-oxidoestra-4-en-3-one
(Example 9)
7β,18-Dimethyl-17α-(1'-propenyl)-17β-3'-oxidoestra-4-en-3-one

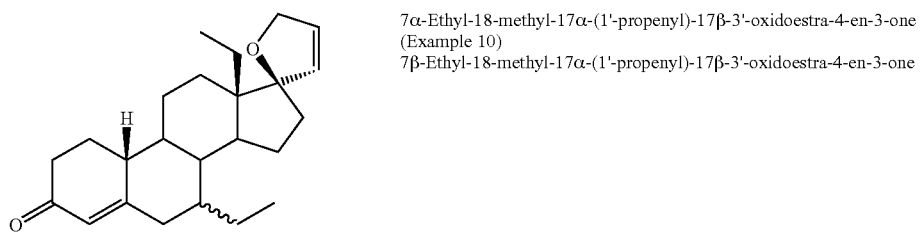

7α-Ethyl-18-methyl-17α-(1'-propenyl)-17β-3'-oxidoestra-4-en-3-one
(Example 10)
7β-Ethyl-18-methyl-17α-(1'-propenyl)-17β-3'-oxidoestra-4-en-3-one

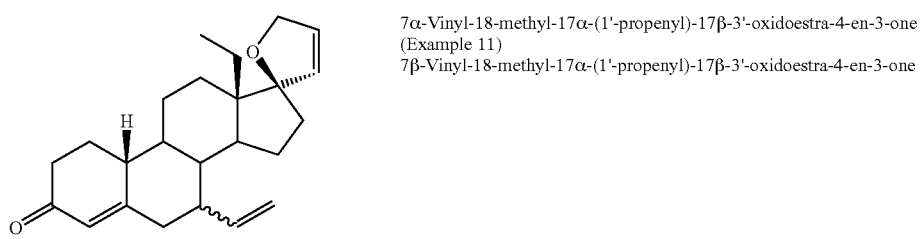

7α-Vinyl-18-methyl-17α-(1'-propenyl)-17β-3'-oxidoestra-4-en-3-one
(Example 11)
7β-Vinyl-18-methyl-17α-(1'-propenyl)-17β-3'-oxidoestra-4-en-3-one

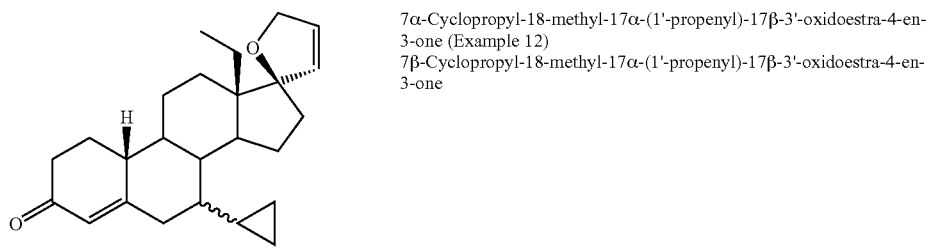

7α-Cyclopropyl-18-methyl-17α-(1'-propenyl)-17β-3'-oxidoestra-4-en-3-one (Example 12)
7β-Cyclopropyl-18-methyl-17α-(1'-propenyl)-17β-3'-oxidoestra-4-en-3-one

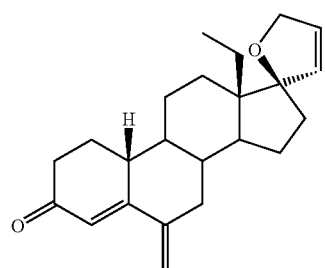

6-Methylene-17α-(1'-propenyl)-18-methyl-17β-3'-oxidoestra-4-en-3-one

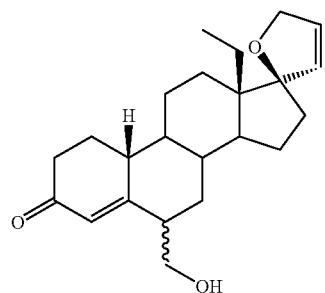

6α-Hydroxymethylene-17α-(1'-propenyl)-18-methyl-17β-3'-oxidoestra-4-en-3-one
6β-Hydroxymethylene-17α-(1'-propenyl)-18-methyl-17β-3'-oxidoestra-4-en-3-one (Example 13)

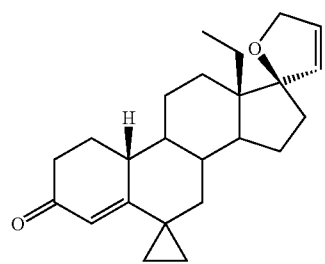

6,6-(1,2-Ethanediyl)-17α-(1'-propenyl)-18-methyl-17β-3'-oxidoestra-4-en-3-one

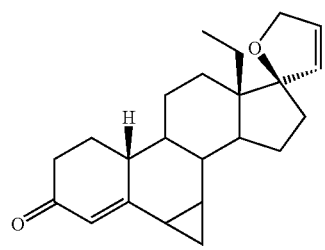

6α,7α-Methylene-17α-(1'-propenyl)-18-methyl-17β-3'-oxidoestra-4-en-3-one
6β,7β-Methylene-17α-(1'-propenyl)-18-methyl-17β-3'-oxidoestra-4-en-3-one

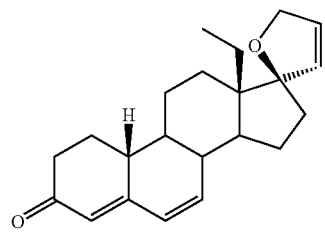

17α-(1'-Propenyl)-18-methyl-17β-3'-oxidoestra-4,6-dien-3-one (Example 8)

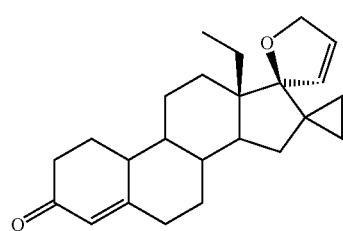

16,16-(1,2-Ethanediyl)-17α-(1'-propenyl)-18-methyl-17β-3'-oxidoestra-4-en-3-one

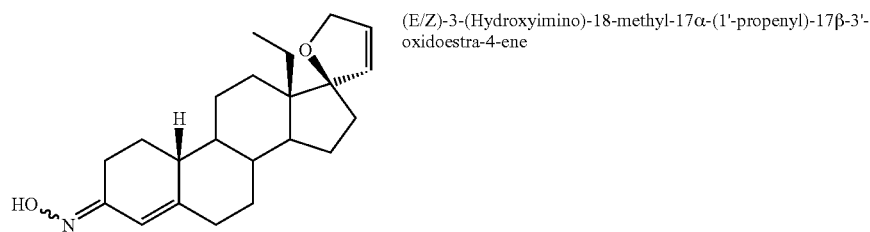 (E/Z)-3-(Hydroxyimino)-18-methyl-17α-(1'-propenyl)-17β-3'-oxidoestra-4-ene

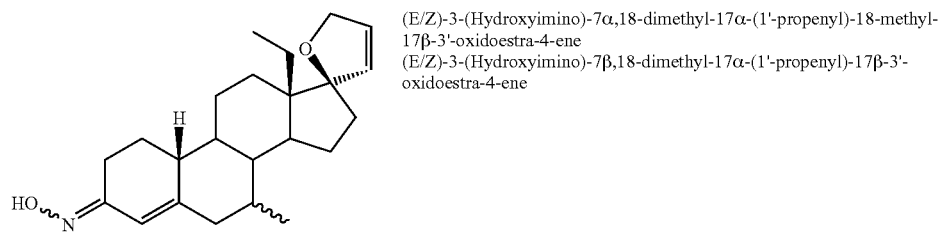 (E/Z)-3-(Hydroxyimino)-7α,18-dimethyl-17α-(1'-propenyl)-18-methyl-17β-3'-oxidoestra-4-ene
(E/Z)-3-(Hydroxyimino)-7β,18-dimethyl-17α-(1'-propenyl)-17β-3'-oxidoestra-4-ene

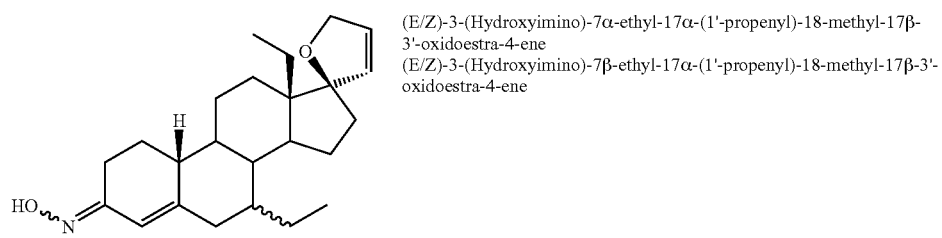 (E/Z)-3-(Hydroxyimino)-7α-ethyl-17α-(1'-propenyl)-18-methyl-17β-3'-oxidoestra-4-ene
(E/Z)-3-(Hydroxyimino)-7β-ethyl-17α-(1'-propenyl)-18-methyl-17β-3'-oxidoestra-4-ene

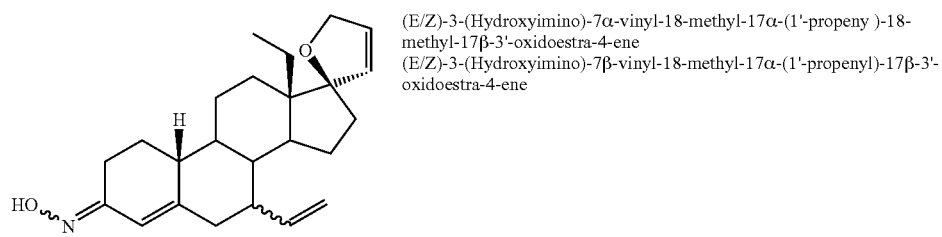 (E/Z)-3-(Hydroxyimino)-7α-vinyl-18-methyl-17α-(1'-propeny )-18-methyl-17β-3'-oxidoestra-4-ene
(E/Z)-3-(Hydroxyimino)-7β-vinyl-18-methyl-17α-(1'-propenyl)-17β-3'-oxidoestra-4-ene

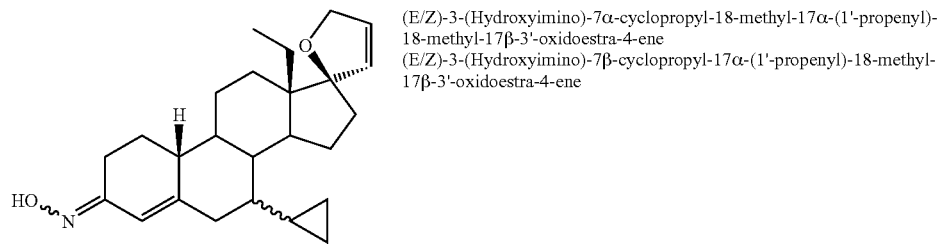 (E/Z)-3-(Hydroxyimino)-7α-cyclopropyl-18-methyl-17α-(1'-propenyl)-18-methyl-17β-3'-oxidoestra-4-ene
(E/Z)-3-(Hydroxyimino)-7β-cyclopropyl-17α-(1'-propenyl)-18-methyl-17β-3'-oxidoestra-4-ene

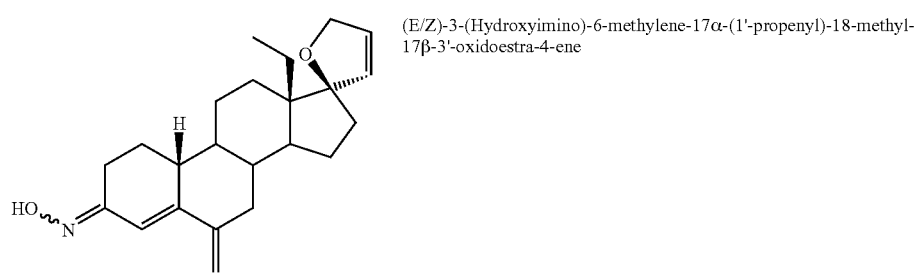 (E/Z)-3-(Hydroxyimino)-6-methylene-17α-(1'-propenyl)-18-methyl-17β-3'-oxidoestra-4-ene

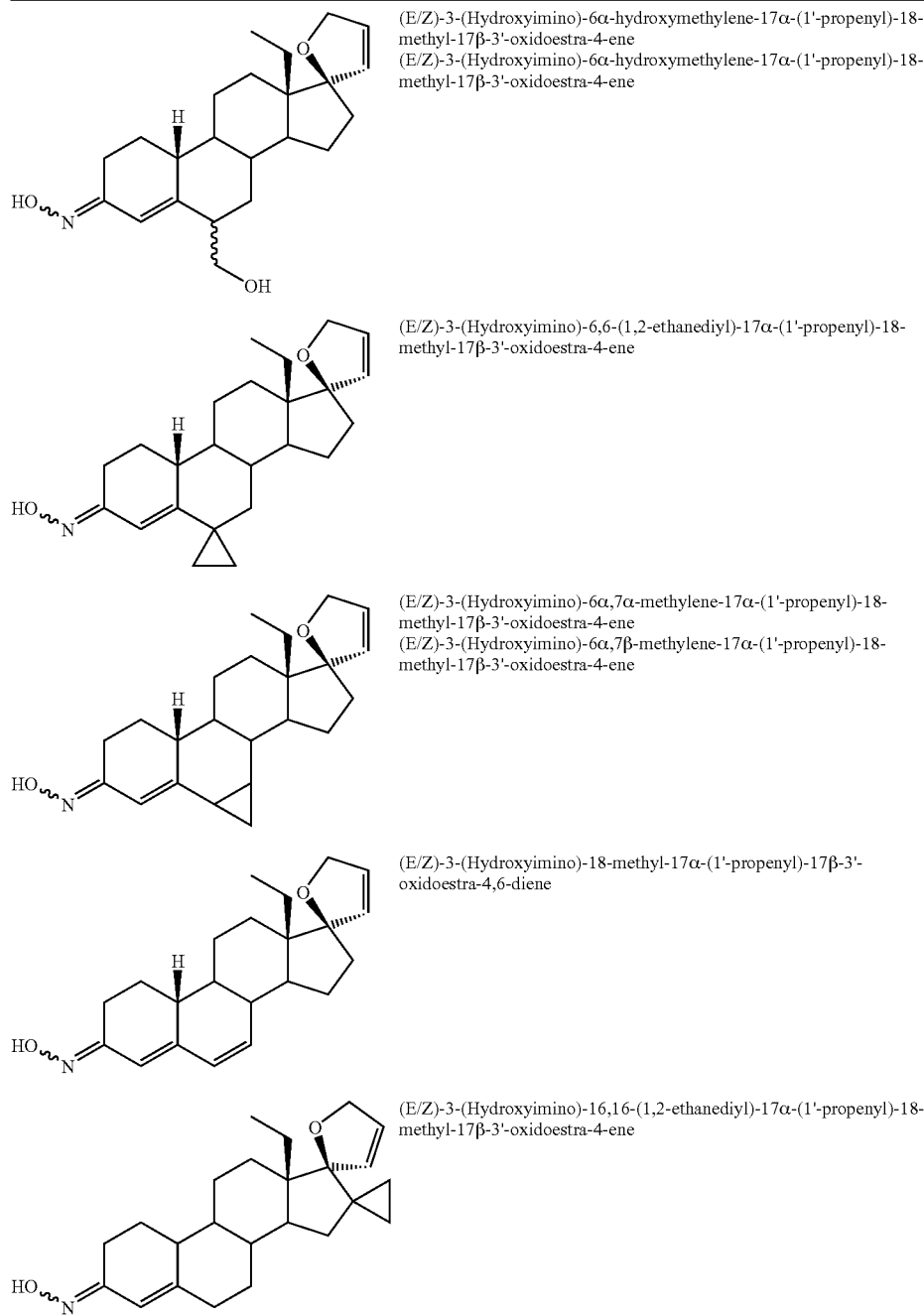

On the basis of their progestational efficacy, the novel compounds with the general chemical formula I can be used alone or in combination with estrogen in medicinal products for contraception.

The derivatives according to the invention are therefore suitable in particular for the production of a medicinal product for oral contraception and for the treatment of pre-, peri- and postmenopausal complaints, including use in preparations for hormone replacement therapy (HRT).

Owing to their favorable action profile, the derivatives according to the invention are moreover especially well suited to the treatment of premenstrual complaints, such as headaches, depressive moods, water retention and mastodynia.

The use of the derivatives according to the invention is especially preferred for the production of a medicinal product with progestational, and preferably also antimineralocorticoid and neutral to slightly androgenic action.

Treatment with the derivatives according to the invention is preferably applied to humans, but can also be carried out on related mammalian species, for example dogs and cats.

For use of the derivatives according to the invention as medicinal products, they are combined with at least one suitable pharmaceutically harmless additive, for example a carrier. The additive is for example suitable for parenteral, preferably oral, application. Relevant materials are pharmaceutically suitable organic or inorganic inert additives, for example water, gelatin, gum arabic, lactose, starch, magnesium stearate, talc, vegetable oils, polyalkylene glycols etc. The medicinal products can be in solid form, for example as tablets, coated tablets, suppositories, capsules, or in liquid form, for example as solutions, suspensions or emulsions. Optionally they also contain excipients, such as preservatives, stabilizers, wetting agents or emulsifiers, salts for altering the osmotic pressure or buffers. For parenteral application, oily solutions are suitable in particular, for example solutions in sesame oil, castor oil and cottonseed oil. To increase the solubility, solubilizers can be added, for example benzyl benzoate or benzyl alcohol. It is also possible to incorporate the derivatives according to the invention in a transdermal system and therefore apply them transdermally. For oral application, consideration may be given in particular to tablets, coated tablets, capsules, pills, suspensions or solutions.

Further examples of administration routes are intravaginal or intrauterine administration. This is possible with physiologically tolerated solutions such as, for example, an aqueous or oily solution with or without suitable solubilizers, dispersants or emulsifiers. Examples of suitable oils are peanut oil, cottonseed oil, castor oil or sesame oil. The selection is by no means restricted thereto.

For intravaginal or intrauterine administration it is possible to use special systems such as an intravaginal system (e.g. vaginal ring, VRS) or an intrauterine system (IUS) which release an active substance of the present invention from a reservoir over a prolonged period (e.g. 1, 2, 3, 4 or 5 years).

A representative example of an intrauterine system which may be mentioned is MIRENA®. This is a T-shaped, levonorgestrel-releasing intrauterine system from Bayer Schering Pharma AG.

Administration is further possible via an implanted depot system composed of an inert carrier material such as, for example, a biodegradable polymer or a synthetic silicone polymer. These depot systems release the active ingredient in a controlled manner over a prolonged period (e.g. 3 months to 3 years) and are implanted subcutaneously.

The dosage of the derivatives according to the invention in contraceptive preparations should be 0.01 to 10 mg per day. The daily dose in the treatment of premenstrual complaints is around 0.1 to 20 mg. The progestational derivatives according to the invention are preferably administered orally in contraceptive preparations and in medicinal products for the treatment of premenstrual complaints. The daily dose is preferably administered as a single dose. The aforementioned dosages relate to oral administration forms.

On use of a depot formulation, the appropriate dosage, equivalent to the aforementioned oral dosages, is released continuously each day from the depot systems described above and employed in the long term.

The progestational and estrogenic active components are preferably applied together orally in contraceptive preparations. The daily dose is preferably administered as a single dose.

As estrogens, consideration may be given to synthetic estrogens, preferably ethinylestradiol, but also mestranol, and natural estrogens, including phytoestrogens.

The estrogen is administered in a daily amount that corresponds to the pharmacological action of 0.01 to 0.04 mg ethinylestradiol. This amount relates to an oral administration form. If a different administration route is chosen, an appropriate dosage amount equivalent to the aforementioned oral dosage is to be used.

As estrogens in medicinal products for the treatment of pre-, peri- and postmenopausal complaints and for hormone replacement therapy, natural estrogens are mainly used, in particular estradiol, but also the esters of estradiol, for example estradiol valerate, or also conjugated estrogens (CEEs=conjugated equine estrogens).

The progestational, antimineralocorticoid and androgenic or antiandrogenic action of the compounds according to the invention was investigated by the following methods:

1. Progesterone Receptor Binding Test:

Using cytosol from progesterone receptor-expressing insect cells (Hi5), competitive binding to the progesterone receptor was determined from the ability to displace $^3$H-progesterone as reference substance from the receptor. If a compound has an affinity corresponding to progesterone, this corresponds to a competition factor (CF) of 1. CF values greater than 1 are characterized by a lower affinity for the progesterone receptor, and CF values of less than 1 are characterized by higher affinity.

2. Mineralocorticoid Receptor Binding Test:

The test was carried out as in 1., with the following modifications: cytosol from mineralocorticoid receptor-expressing insect cells (Hi5) was used, and the reference substance was $^3$H-aldosterone.

3. Androgen Receptor Binding Test:

The test was carried out as in 1., with the following modifications: cytosol from androgen receptor-expressing insect cells (Hi5) was used, and the reference substance was $^3$H-testosterone.

The results of the binding tests and the ratio of the competition factors CF(PR) and CR(MR) are shown in Table 1, which for comparison also shows receptor binding values of drospirenone as reference substance A.

4. Determination of Progestational Action by Means of Transactivation Tests:

The culture medium used for culture of the cells used for the assay was DMEM (Dulbecco's Modified Eagle Medium: 4500 mg/ml glucose; PAA, #E15-009) with 10% FCS (Biochrom, S0115, batch #615B), 4 mM L-glutamine, 1% penicillin/streptomycin, 1 mg/ml 6418 and 0.5 μg/ml puromycin.

Reporter cell lines (CHO K1 cells stably transfected with a fusion protein from the PR-ligand-binding domain and a Gal4-transactivation domain and a reporter construct, which contained luciferase under the control of a Gal4-responsive promoter) were seeded at a density of $4 \times 10^4$ cells per well in white, opaque tissue culture plates each with 96 wells (PerkinElmer, #P12-106-017) and kept in culture medium with 3% DCC-FCS (serum treated with activated charcoal to remove interfering components contained in the serum). The test compounds were added eight hours later, and the cells were incubated with the compounds for 16 hours. The tests were carried out in triplicate. At the end of incubation the medium containing the effector was removed and replaced with lysis buffer. After luciferase assay substrate (Promega, #E1501) had been added, the 96-well plates were then put in a microplate luminometer (Pherastar, BMG Labtech), and the luminescence was measured. The $IC_{50}$ values were evaluated using software for calculating dose-effect relations. Table 2 presents the test results and, for comparison, corresponding results for drospirenone as reference substance A.

5. Determination of Antimineralocorticoid Action by Means of Transactivation Tests:

The antimineralocorticoid activity of the test substances was determined as for the transactivation tests described above.

The following modifications were undertaken: In this case reporter cell lines were used (MDCK cells) that express the human mineralocorticoid receptor, and transiently contain a reporter construct that contains luciferase under the control of a steroid hormone-responsive promoter.

The culture medium used for cultivation of the cells used for the assay was DMEM EARLE'S MEM (PAA, Cat.: E15-025) provided with 100U penicillin/0.1 mg/ml streptomycin (PAA, Cat: P11-010), 4 mM L-glutamine (PAA, Cat: M11-004) and fetal calf serum (BIO Witthaker, Cat: DE14-801F).

For determination of antimineralocorticoid efficacy, 1 nM aldosterone (SIGMA A-6628, Lot 22H4033) was added to the cells, to achieve almost maximum stimulation of the reporter gene. Inhibition of the effect indicated a mineralocorticoid-antagonistic action of the substances (Table 2; for comparison, corresponding values for drospirenone (A)).

6. Determination of Androgenic/Antiandrogenic Action by Means of Transactivation Tests:

The androgenic/antiandrogenic action of the test substances was determined as for the transactivation tests described above.

The following modifications were made: In this case reporter cell lines were used (PC3 cells) that express the androgen receptor, and a reporter construct that contains luciferase under the control of a steroid hormone-responsive promoter.

The culture medium used for cultivation of the cells used for the assay was RPMI medium without phenol red (PAA, #E15-49), provided with 100U penicillin/0.1 mg/ml streptomycin (PAA, Cat: P11-010), 4 mM L-glutamine (PAA, Cat: M11-004) and fetal calf serum (BIO Witthaker, Cat: DE14-801F).

For determination of the antiandrogenic efficacy, 0.05 nM R1881 was added to the cells, in order to achieve almost maximum stimulation of the reporter gene. Inhibition of the effect indicated an androgen-antagonistic action of the substances (Table 2; for comparison, corresponding values for drospirenone (A)).

If the production of the starting compounds is not described here, these are known to a person skilled in the art or can be prepared similarly to known compounds or methods described here. The isomeric mixtures can be separated into the individual compounds by the usual methods, for example crystallization, chromatography or salt formation. The salts are prepared in the usual way, by adding, to a solution of the compounds with the general chemical formula I, the equivalent amount or an excess of a base or acid, which is optionally in solution, if necessary separating the precipitate or processing the solution in the usual way.

The compounds with the general chemical formula I are prepared, starting from compounds with the general chemical formula 1a (Scheme 2) or 1b (Scheme 3), according to the methods shown in Scheme 1 in which $R^4$, $R^{6a}$, $R^{6b}$, $R^7$, $R^{15}$, $R^{18}$ and Z have the meanings stated previously and $R^6$, $R^7$ in 8b together form oxygen or a methylene group, $R^{16a}$, $R^{16b}$ in 32a and 40a together form methylene, in 32b and 40b together form 1,2-ethanediyl, in 32c and 40c, each independently of one another, are selected from the group comprising hydrogen and $C_1$-$C_{10}$-alkyl, U is oxygen, two alkoxy groups $OR^{19}$, a $C_2$-$C_{10}$-alkylene-α,ω-dioxy group, which can be linear or branched, and $R^{19}$ stands for a $C_1$-$C_{20}$-alkyl residue, $R^{20}$ is a $C_1$-$C_{20}$-alkyl residue, X is an $NR^{21a}R^{21b}$ group or an alkoxy group $OR^{22}$, $R^{21a}$, $R^{21b}$ each independently of one another are selected from the group comprising hydrogen and $C_1$-$C_{10}$-alkyl, or together form a $C_4$-$C_{10}$-α,ω-alkylene group, which can be linear or branched and $R^{22}$ is a $C_1$-$C_{20}$-alkyl residue.

For a person skilled in the art it is obvious that in the descriptions of the synthetic transformations it is always assumed that if necessary other functional groups present on the steroid structure are suitably protected.

The introduction of a 6,7-double bond with formation of compounds with the general chemical formulae 5, 8a, 10 or 12 is carried out by bromination of the respective 3,5-dienol ethers 4, 7, 9 or 11 followed by elimination of hydrogen bromide (see for example J. Fried, J. A. Edwards, *Organic Reactions in Steroid Chemistry*, Van Nostrand Reinhold Company 1972, p. 265-374).

The dienol ether bromination of compounds 4, 7, 9 or 11 can for example be carried out analogously to the specification from *Steroids* 1, 233 (1963). Hydrogen bromide elimination with formation of the compounds with the general chemical formulae 5, 8a, 10 or 12 is achieved by heating the 6-bromo compound with basic reagents, for example with LiBr or $Li_2CO_3$, in aprotic solvents, such as dimethylformamide, at temperatures of 50-120° C. or alternatively by heating the 6-bromo compounds in a solvent, such as collidine or lutidine.

The introduction of a substituent $R^4$ can be carried out, for example, starting from a compound with one of the general chemical formulae 3, 5, 6, 8a, 8b or 10, by epoxidation of the 4,5-double bond with hydrogen peroxide under alkaline conditions and reaction of the resultant epoxides in a suitable solvent with acids with the general chemical formula H—$R^4$, where $R^4$ can be a halogen atom, preferably chlorine or bromine. Compounds in which $R^4$ has the meaning bromine can for example be reacted with 2,2-difluoro-2-(fluorosulfonyl) methyl acetate in dimethylformamide in the presence of copper(I) iodide to form compounds in which $R^4$ has the meaning fluorine. Alternatively, starting from a compound with one of the general chemical formulae 3, 5, 6, 8a, 8b or 10, halogen can be introduced directly by reaction with sulfuryl chloride or sulfuryl bromide in the presence of a suitable base, for example pyridine, with $R^4$ having the meaning chlorine or bromine.

Compound 5 or 12 is converted by methenylation of the 6,7-double bond by known methods, for example with dimethylsulfoxonium methylide (see for example DE-A 11 83 500, DE-A 29 22 500, EP-A 0 019 690, U.S. Pat. No. 4,291, 029; *J. Am. Chem. Soc.* 84, 867 (1962)) to a compound 8b or 13 ($R^6$, $R^7$ together form a methylene group), obtaining a mixture of the α- and β-isomers, which can be separated into the individual isomers for example by chromatography.

Compounds of type 8b or 13 can be obtained as described in the examples or similarly to these specifications, using similar reagents to those described there.

Synthesis of the spirocydic compound 10 ($R^{6a}$, $R^{6b}$ together form 1,2-ethanediyl) starts from compound 3 or 6, which are first converted to a 3-amino-3,5-diene derivative 7 (X=NR$^{21a}$R$^{21b}$). By reaction with formalin in alcoholic solution, the 6-hydroxymethylene derivative 8a (R$^6$=hydroxymethylene) is obtained. After converting the hydroxyl group into a leaving group, such as a mesylate, tosylate or even benzoate, compound 10 can be prepared by reaction with trimethylsulfoxonium iodide using bases, such as alkali hydroxides, alkali alcoholates, in suitable solvents, such as dimethyl sulfoxide.

For introduction of a 6-methylene group, compound 8a (R$^6$=hydroxymethylene) can be dehydrated with for example hydrochloric acid in dioxane/water. Compound 10 (R$^{6a}$, R$^{6b}$ together form methylene) can also be produced after converting the hydroxyl group into a leaving group, such as a mesylate, tosylate or even benzoate (see DE-A 34 02 329, EP-A 0 150 157, U.S. Pat. No. 4,584,288; *J. Med, Chem.* 34, 2464 (1991)), Another possibility for the production of 6-methylene compounds 10 is the direct reaction of the 4(5)-unsaturated 3-ketones, for example compound 8a (R$^6$=hydrogen), with formaldehyde acetals in the presence of sodium acetate with for example phosphorus oxychloride or phosphorus pentachloride in suitable solvents, such as chloroform (see for example K. Annen, H, Hofmeister, H. Laurent and R. Wiechert, *Synthesis* 34 (1982)).

The 6-methylene compounds can be used for the preparation of compounds with the general chemical formula 10, in which R$^{6a}$ is methyl and R$^{6b}$ and R$^7$ drop out with formation of a double bond between C$^6$ and C$^7$.

For this it is possible for example to use a method described in *Tetrahedron* 21, 1619 (1965), in which isomerization of the double bond is achieved by heating the 6-methylene compounds in ethanol with 5% palladium/charcoal catalyst, pretreated either with hydrogen or by heating with a small amount of cyclohexene. The isomerization can also be carried out with a catalyst that has not been pretreated, if a small amount of cyclohexene is added to the reaction mixture. The formation of small proportions of hydrogenated products can be prevented by adding an excess of sodium acetate.

Alternatively, compound 9 (X=OR$^{22}$) can be used as precursor. The direct preparation of 6-methyl-4,6-dien-3-one derivatives has been described (see K. Annen, H. Hofmeister, H. Laurent and R. Wiechert, *Lieb. Ann.* 712 (1983)).

Compounds 10 in which R$^{6b}$ represents an a-methyl function can be prepared in suitable conditions from the 6-methylene compounds (10: R$^{6a}$, R$^{6b}$ together form methylene) by hydrogenation. The best results (selective hydrogenation of the exo-methylene function) are achieved by transfer-hydrogenation (*J. Chem. Soc.* 3578 (1954)). If the 6-methylene derivatives 10 are heated in a suitable solvent, for example ethanol, in the presence of a hydride donor, for example cyclohexene, then 6α-methyl derivatives are obtained at very good yields. Small proportions of 6β-methyl compound can be isomerized in acid conditions (*Tetrahedron* 1619 (1965)).

The selective preparation of 6β-methyl compounds is also possible. For this, the 4-en-3-ones, such as compound 8a, are reacted for example with ethylene glycol, trimethyl orthoformate in dichloromethane in the presence of catalytic amounts of an acid, for example p-toluenesulfonic acid, to give the corresponding 3-ketals. During this ketalization there is isomerization of the double bond into position C$^5$. Selective epoxidation of this 5-double bond is achieved for example by using organic per-acids, for example m-chloroperbenzoic acid, in a suitable solvent, such as dichloromethane. As an alternative, the epoxidation can also be carried out with hydrogen peroxide in the presence of for example hexachloroacetone or 3-nitrotrifluoroacetophenone. The 5,6α-epoxides formed can then be opened axially using appropriate alkylmagnesium halides or alkyllithium compounds. In this way, 5α-hydroxy-6β-alkyl compounds are obtained. The 3-keto protecting group can be cleaved, obtaining the 5α-hydroxy function, by treatment in mild acidic conditions (acetic acid or 4N hydrochloric acid at 0° C.). Basic elimination of the 5α-hydroxy function with for example dilute aqueous sodium hydroxide solution yields the 3-keto-4-ene compounds with a 6-alkyl group in the β position. Alternatively, cleavage of the ketal in harsher conditions (with aqueous hydrochloric acid or another strong acid) yields the corresponding 6α-alkyl compounds.

The introduction of a 7-alkyl, 7-alkenyl or 7-alkynyl group to form compounds with the general chemical formula 6 is effected by 1,6-addition of a corresponding organometallic compound to the precursor with the general chemical formula 5 under the action of copper salts. Divalent metals, such as magnesium and zinc, are preferred; chlorine, bromine and iodine are preferred as counterions. Suitable copper salts are monovalent or divalent copper compounds, for example copper chloride, copper bromide or copper acetate. The reaction takes place in an inert solvent, for example, tetrahydrofuran, diethyl ether or dichloromethane.

The compounds 3, 5, 6, 8a, 8b, 10, 11 or 12 obtained, in which Z stands for an oxygen atom, can be converted by reaction with hydroxylamine hydrochloride, alkyloxyamine hydrochlorides or sulfonyl hydrazines in the presence of a tertiary amine at temperatures between −20 and +40° C. to their corresponding E/Z-configured oximes or sulfonyl hydrazones (general formula I with Z denoting NOR', NNHSO$_2$R'). Suitable tertiary bases are for example trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), pyridine being preferred. An analogous method is described for example in WO 98/24801 A for the production of corresponding 3-oxyimino derivatives of drospirenone.

For the preparation of an end product with the general chemical formula I with Z denoting two hydrogen atoms, the 3-oxo group can be removed for example following the instructions given in DE-A 28 05 490 by reductive cleavage of a thioketal of the 3-keto compound on a suitable precursor, for example compounds of the general formulae 3, 5, 6, 8a, 8b, 10, 11 or 12.

The formation of spiroethers to compounds with one of the general chemical formulae 6 or 11 is carried out starting from the corresponding 17-hydroxypropenyl compounds 5 or 10, by converting the primary hydroxyl group to a leaving group and subsequent intramolecular substitution. Halogen atoms, for example chlorine, bromine or iodine, and alkyl-, aryl- or aralkylsulfonates, for example methanesulfonate, phenylsulfonate, tolylsulfonate, trifluoromethanesulfonate, nonafluorobutanesulfonate, are suitable as leaving group. The intramolecular cyclization to the spiroether can be carried out by deprotonation of the tertiary hydroxyl group with suitable bases, for example triethylamine, diethylamine, diisopropylethylamine, pyridine, dimethylaminopyridine, sodium hydride, sodium hexamethyldisilazane, potassium hexamethyldisilazane, potassium tert.-butanolate or n-butyllithium. Methods and conditions permitting introduction of the leaving group with direct intramolecular cyclization in one reaction vessel are preferred.

Scheme 1
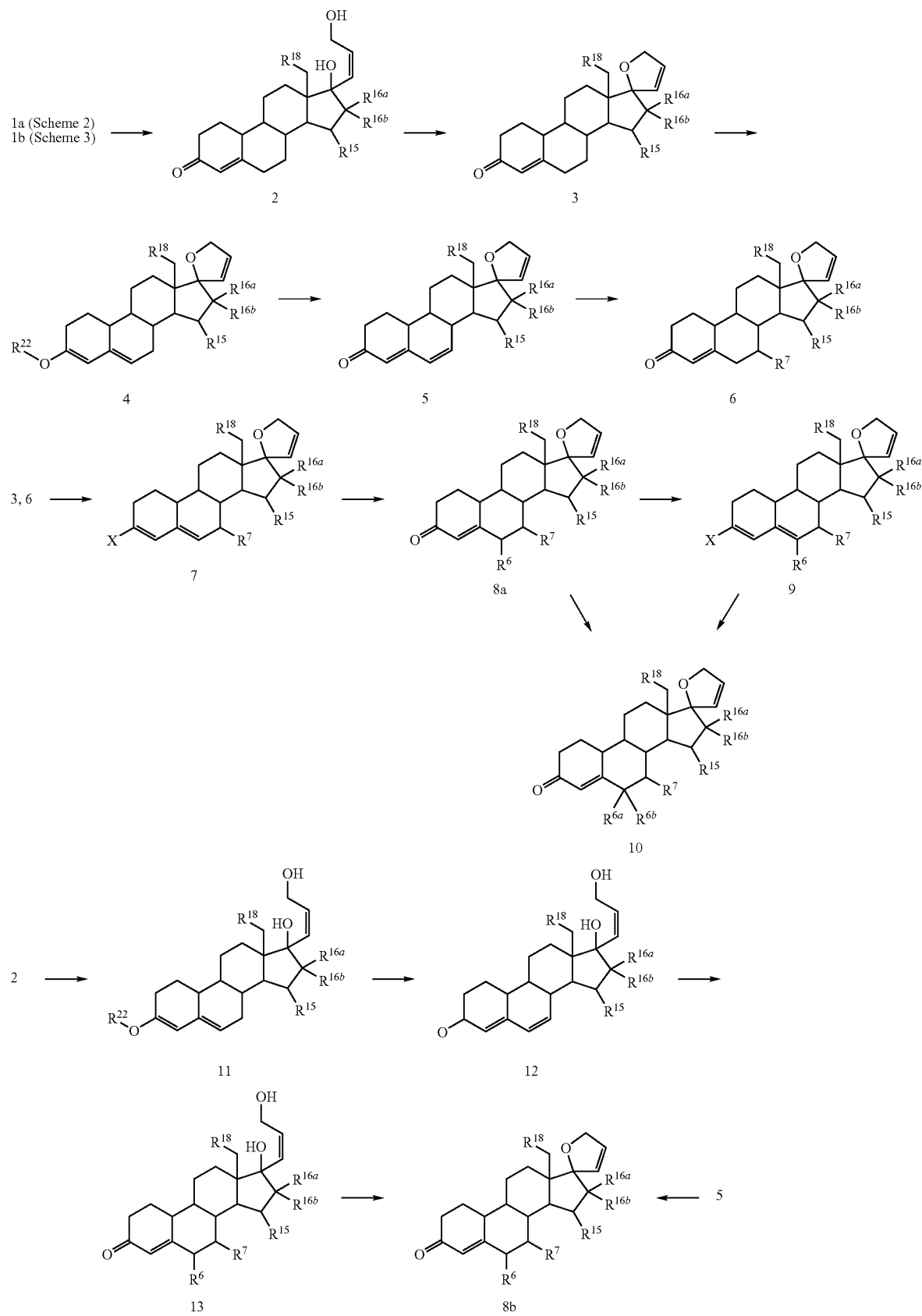

-continued

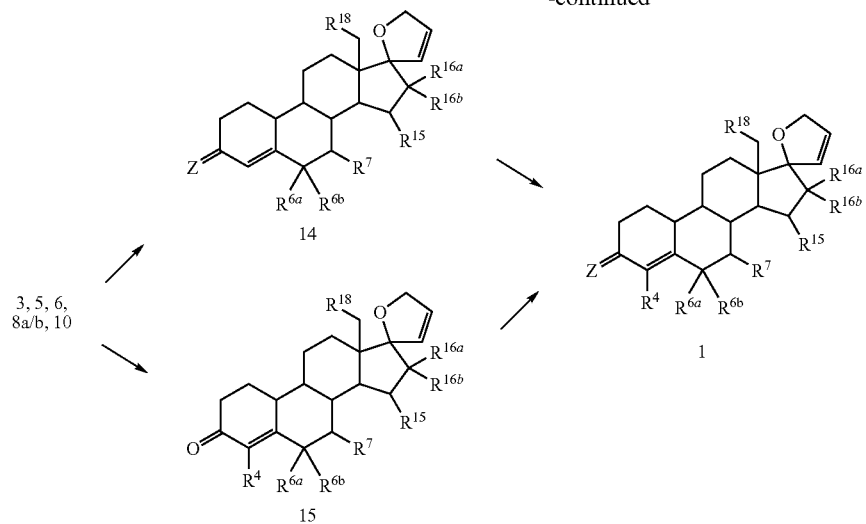

Compounds with the general chemical formula 1 a are prepared according to the methods presented in Scheme 2, in which $R^{15}$ and $R^{18}$ have the meanings stated previously and $R^{16a}$, $R^{16b}$ in 32a together form methylene, in 32b together form 1,2-ethanediyl, in 32c each independently of one another are selected from the group comprising hydrogen and $C_1$-$C_{10}$-alkyl, $R^{20}$ is a $C_1$-$C_{20}$-alkyl residue.

Compounds 30 to 1a in Scheme 2 each have a double bond between $C^5$ and $C^6$ or between $C^5$ and $C^{10}$ and another double bond between $C^2$ and $C^8$ or between $C^3$ and $C^4$.

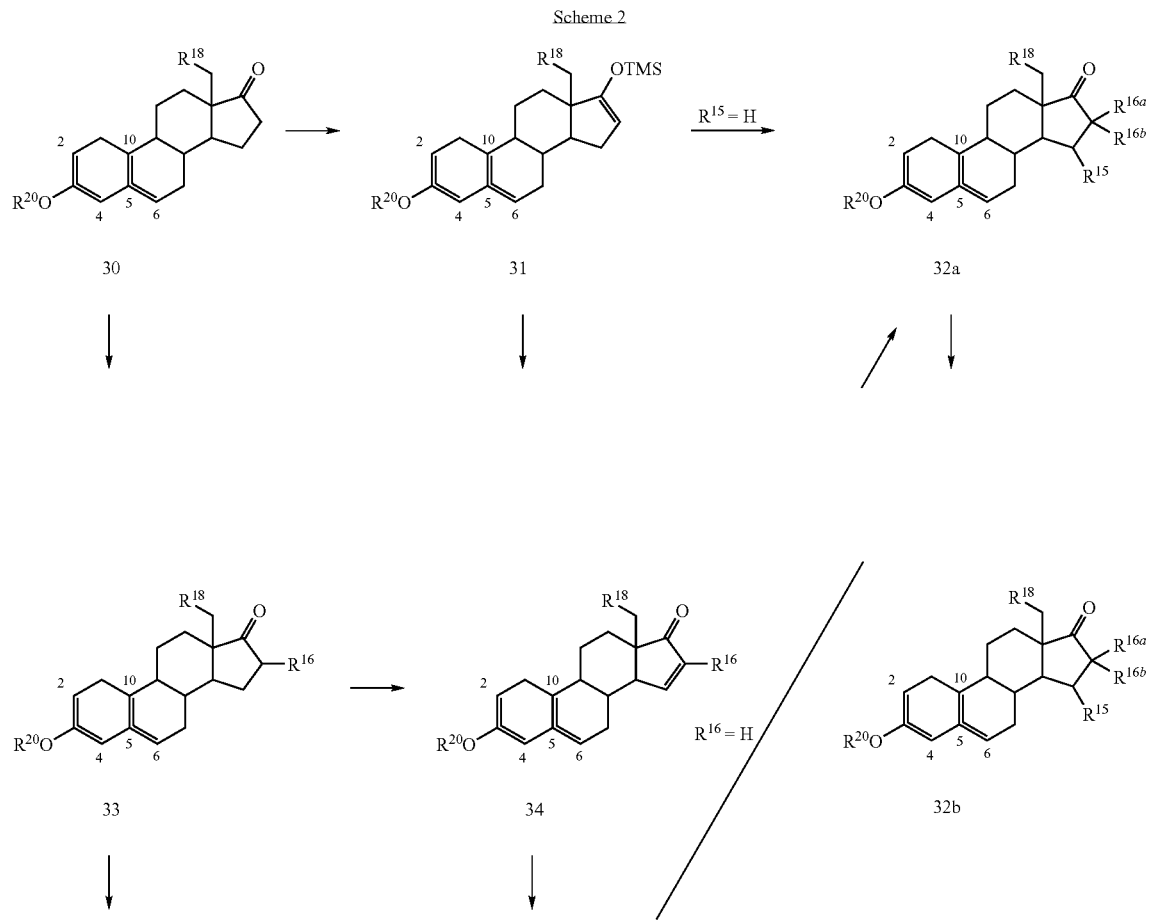

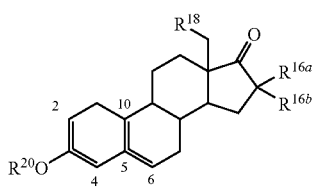

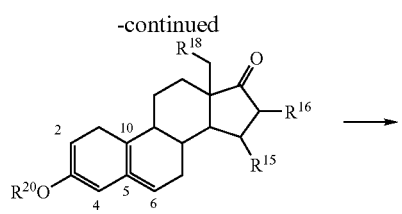

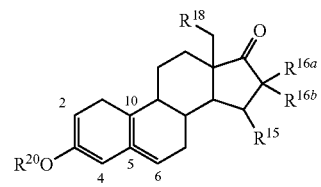

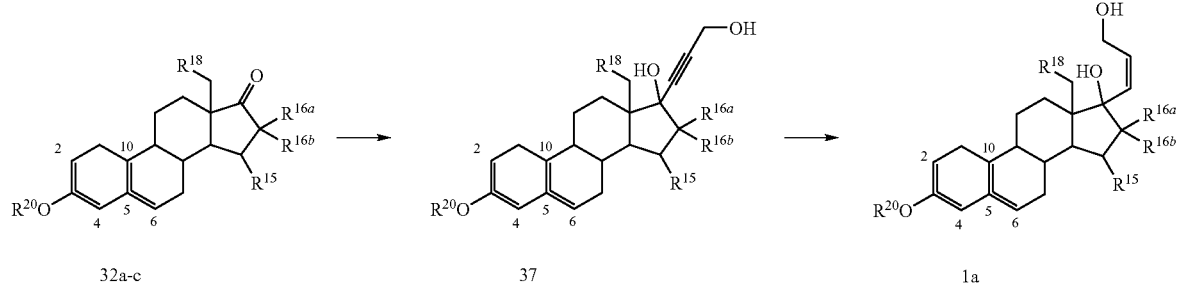

Compounds with the general chemical formula 1b are prepared according to the methods presented in Scheme 3, in which $R^{15}$ and $R^{18}$ have the meanings stated previously and $R^{16a}$, $R^{16b}$ in 40a together form methylene, in 40b together form 1,2-ethanediyl, in 40c each independently of one another are selected from the group comprising hydrogen and $C_1$-$C_{10}$-alkyl, U is oxygen, two alkoxy groups $OR^{19}$, a $C_2$-$C_{10}$-alkylene-α,ω-dioxy group, which can be linear or branched, where $R^{19}$ stands for a $C_1$-$C_{20}$-alkyl residue.

Compounds 38 to 1b in Scheme 3 each have a double bond between $C^4$ and $C^5$ or between $C^5$ and $C^6$ or between $C^5$ and $C^{10}$.

Scheme 3

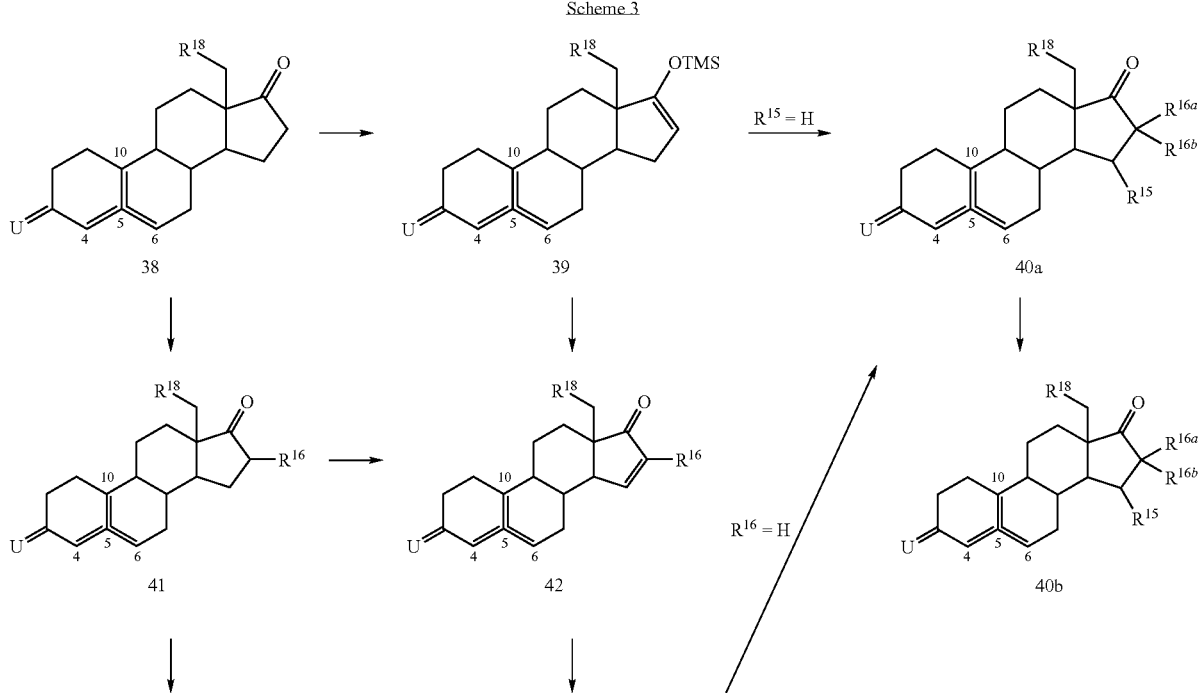

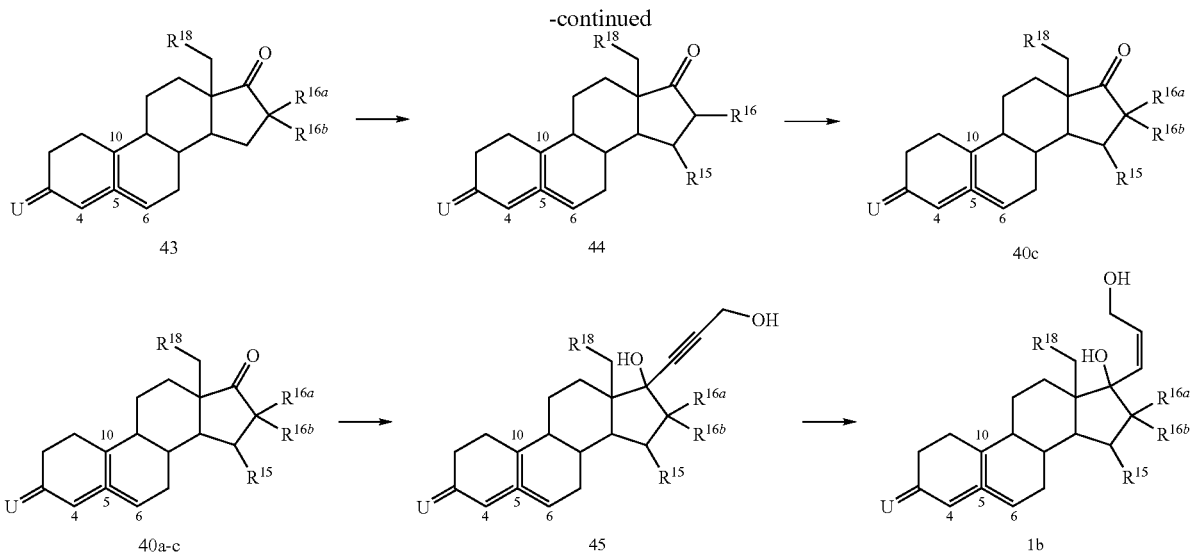

The following examples are provided for further explanation of the invention, without it being limited to the examples shown:

Example 1

Spiroether Formation

17α-(1'-Propenyl)-17β-3'-oxidoestra-4-en-3-one

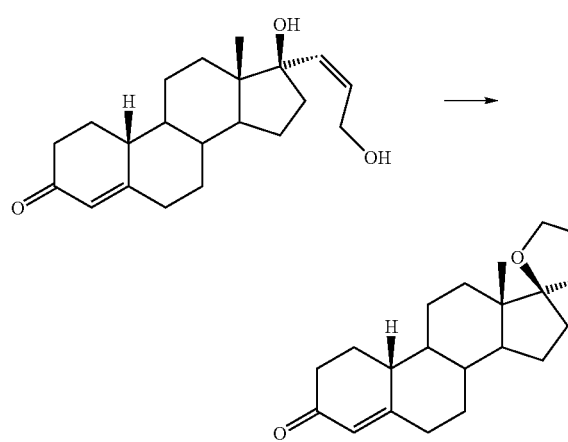

43.6 ml triethylamine and 15.2 g p-toluenesulfonic acid chloride are added, at 3° C., to a solution of 10 g of the compound prepared according to Example 1a in 600 ml dichloromethane, it is heated to 23° C. and stirred for 15 hours. It is poured into saturated sodium hydrogencarbonate solution, extracted with ethyl acetate several times, the combined organic extracts are washed with water and saturated sodium chloride solution and dried over sodium sulfate. The residue obtained after filtration and removal of the solvent is purified by chromatography. 7.93 g of the title compound is isolated.

$^1$H-NMR (CDCl$_3$): δ=0.87 (1H), 1.00 (3H), 1.07 (1H), 1.14-1.96 (11H), 2.06 (1H), 2.13 (1H), 2.23-2.37 (3H), 2.44 (1H), 2.52 (1H), 4.53-4.66 (2H), 5.81-5.90 (3H) ppm.

Example 1a

Ketal Cleavage

17α(Z)-(3'-Hydroxypropen-1'-yl)-17β-hydroxyestra-4-en-3-one 1.51 ml of 4N hydrochloric acid is added to a solution of 367 mg of the compound prepared according to Example 1b in 30 ml acetone and stirred for 30 minutes at 23° C. It is poured into saturated sodium hydrogencarbonate solution, extracted with ethyl acetate several times, the combined organic extracts are washed with saturated sodium chloride solution and dried over sodium sulfate. The residue obtained after filtration and removal of the solvent is purified by chromatography. 269 mg of the title compound is isolated.

Example 1b

Lindlar Hydrogenation

17α(Z)-(3'-Hydroxypropen-1'-yl)-3,3-dimethoxy-17β-hydroxyestra-5(10)-ene

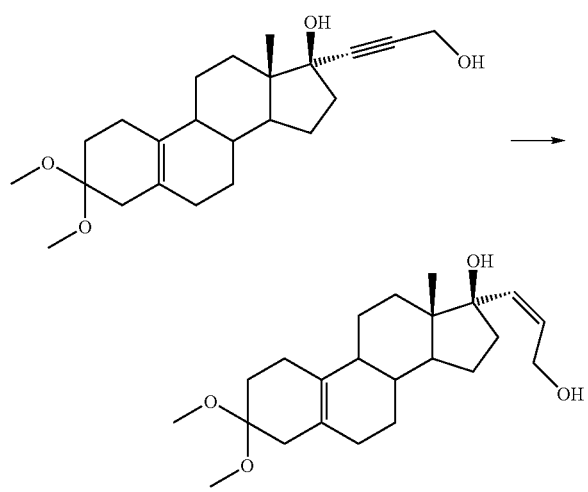

5.35 ml pyridine and 560 mg palladium on barium sulfate are added to a solution of 3.94 g of the compound prepared according to Example 1c in 90 ml tetrahydrofuran and it is hydrogenated in a hydrogen atmosphere. It is filtered on Celite and after concentration by evaporation and chromatography, 3.04 g of the title compound are isolated.

Example 1c

Hydroxypropyne Addition

17α-(3'-Hydroxypropyn-1'-yl)-3,3-dimethoxy-17β-hydroxyestra-5(10)-ene

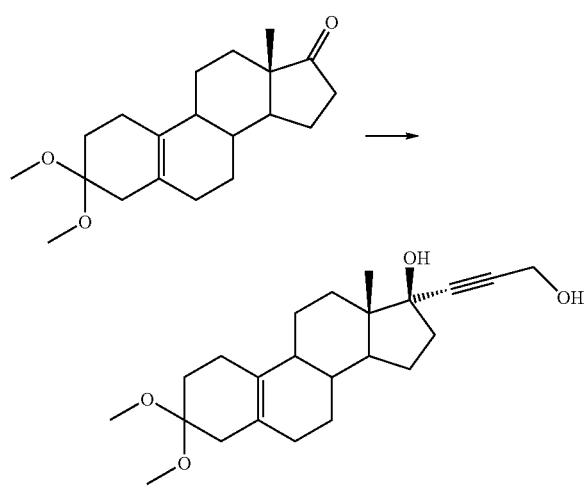

1.13 l of a 2.5-molar solution of butyllithium in hexane is added to a solution of 92.7 ml of 2-propyn-1-ol in 1.4 l tetrahydrofuran at −60° C. After 30 minutes, a solution of 100 g of 3,3-dimethoxy-estra-5(10)-en-17-one in 0.8 l tetrahydrofuran is added, it is allowed to warm up to 23° C. and it is stirred for a further 16 hours. It is poured into water, extracted several times with ethyl acetate, the combined organic extracts are washed with saturated sodium chloride solution and dried over sodium sulfate. The residue obtained after filtration and removal of the solvent is purified by crystallization. 72.9 g of the title compound is isolated.

Example 2

Dienone Formation From Dienol Ether

17α-(1'-Propenyl)-17β-3'-oxidoestra-4,6-dien-3-one

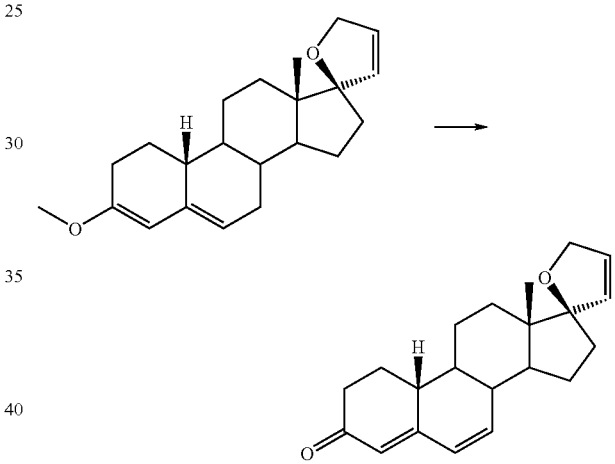

454 mg sodium acetate and 4.5 ml water are added to a solution of 4.0 g of the compound prepared according to Example 2a in 45.4 ml N-methylpyrrolidone, it is cooled to −10° C. and a total of 1.75 g dibromohydantoin is added in portions. After 30 minutes, 1.7 g lithium bromide and 1.49 g lithium carbonate are added and it is heated for 1 hour at a bath temperature of 100° C. It is poured into a mixture of ice and sodium chloride solution and the precipitated product is filtered off with suction. 3.93 g of the title compound is isolated as raw product, which can be reacted further directly or can be further purified by recrystallization.

$^1$H-NMR (CDCl$_3$): δ=0.98 (3H), 1.10 (1H), 1.20 (1H), 1.27-1.38 (2H), 1.45-1.58 (3H), 1.74-1.88 (3H), 2.06 (1H), 2.17 (1H), 2.24-2.39 (3H), 2.54 (1H), 4.51-4.62 (2H), 5.78 (2H), 5.84 (1H), 6.20 (2H) ppm.

Example 2a

Dienol Ether Formation

3-Methoxy-17α-(1'-propenyl)-17β-3'-oxidoestra-3,5-diene

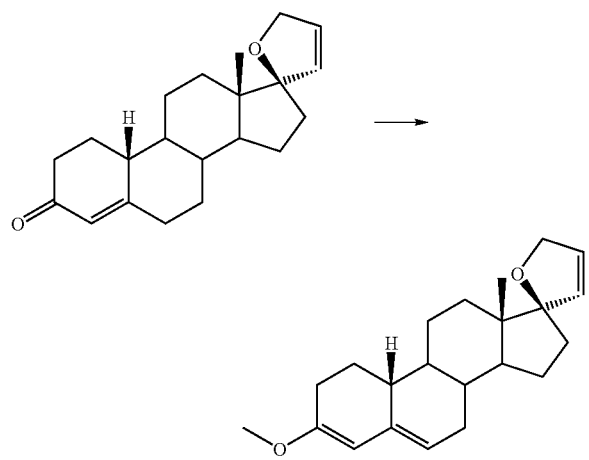

60.3 mg pyridinium p-toluenesulfonate is added to a solution of 500 mg of the compound prepared according to Example 1 in 5.96 ml of 2,2-dimethoxypropane and it is heated under reflux for 2 hours. It is poured into saturated sodium hydrogencarbonate solution, extracted several times with ethyl acetate, the combined organic extracts are washed with saturated sodium chloride solution and dried over sodium sulfate. The residue obtained after filtration and removal of the solvent is purified by recrystallization. 351 mg of the title compound is isolated.

Example 3

1,6-addition

7α-Methyl-17α-(1'-propenyl)-17β-3'-oxidoestra-4-en-3-one (A) and 7β-methyl-17α-(1'-propenyl)-17β-3'-oxidoestra-4-en-3-one (B)

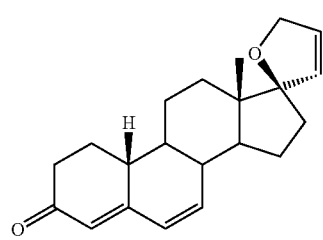

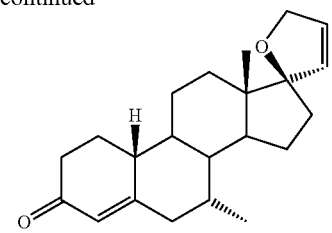

778 μl of a 3-molar solution of methylmagnesium chloride in tetrahydrofuran is added dropwise to a suspension of 18.5 mg copper(I) chloride in 2.9 ml tetrahydrofuran cooled to −30° C., and it is stirred for a further 10 minutes. It is cooled to −25° C. and the solution is added dropwise to 290 mg of the compound prepared according to Example 2 in 3.3 ml tetrahydrofuran. After 10 minutes it is poured into 1N hydrochloric acid, extracted with ethyl acetate several times, the combined organic extracts are washed with saturated sodium chloride solution and dried over sodium sulfate. The residue obtained after filtration and removal of the solvent is purified by chromatography. 148 mg of the title compound A is isolated along with a still contaminated mixture that contains proportions of the title compound B.

$^1$H-NMR (CDCl$_3$) of A: δ=0.78 (3H), 0.97 (3H), 1.08 (1H), 1.15 (1H), 1.22-1.31 (2H), 1.37 (1H), 1.42 (1H), 1.51-1.65 (3H), 1.75 (1H), 1.86 (1H), 1.99-2.06 (3H), 2.24-2.30 (3H), 2.41 (1H), 2.48 (1H), 4.54 (1H), 4.59 (1H), 5.79-5.86 (3H) ppm.

Example 4

7α-Ethyl-17α-(1'-propenyl)-17β-3'-oxidoestra-4-en-3-one (A) and 7β-ethyl-17α-(1'-propenyl)-17β-3'-oxidoestra-4-en-3-one (B)

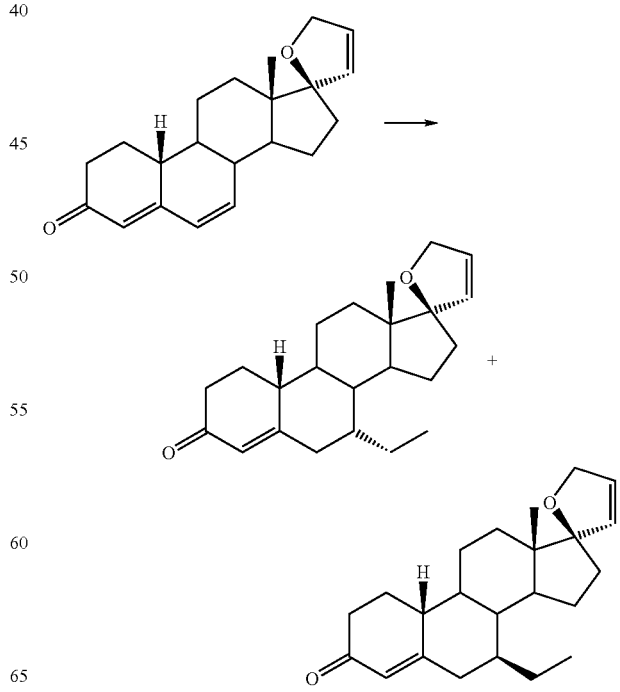

Similarly to Example 3, 550 mg of the compound prepared according to Example 2 using ethylmagnesium chloride is reacted and, after processing and purification, 37 mg of the title compound A and 9 mg of the title compound B are isolated.

$^1$H-NMR (CD$_2$Cl$_2$) of A: δ=0.87 (3H), 0.93 (3H), 0.96-1.09 (2H), 1.14 (1H), 1.23 (1H), 1.30-1.42 (4H), 1.47-1.67 (4H), 1.71 (1H), 1.84 (1H), 1.97 (1H), 2.04 (1H), 2.19-2.35 (4H), 2.55 (1H), 4.48 (1H), 4.52 (1H), 5.77 (1H), 5.83 (2H) ppm.

$^1$H-NMR (CD$_2$Cl$_2$) of B: δ=0.92 (3H), 0.98 (3H), 1.15-1.78 (12H), 1.81-2.42 (8H), 2.51 (1H), 4.54 (2H), 5.79 (1H), 5.85 (2H) ppm.

Example 5

17α-(1'-Propenyl)-7α-vinyl-17β-3'-oxidoestra-4-en-3-one (A) and 17α-(1'-propenyl)-7β-vinyl-17β-3'-oxidoestra-4-en-3-one (B)

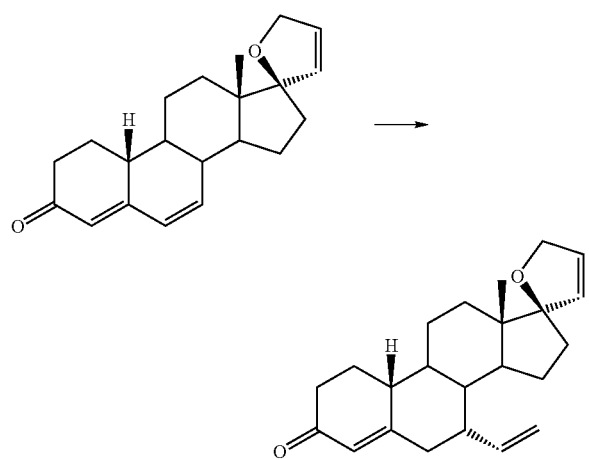

Similarly to Example 3, 550 mg of the compound prepared according to Example 2 using vinylmagnesium chloride is reacted and, after processing and purification, 58 mg of the title compound A is isolated along with a still contaminated mixture that contains proportions of the title compound B.

$^1$H-NMR (CDCl$_3$) of A: δ=0.96 (3H), 1.06-1.45 (6H), 1.49-1.77 (4H), 1.84 (1H), 2.00 (1H), 2.09 (1H), 2.22-2.33 (2H), 2.39-2.48 (2H), 2.50-2.57 (2H), 4.52 (1H), 4.58 (1H), 5.00-5.14 (2H), 5.68-5.86 (4H) ppm.

Example 6

16,16-Ethylene-17α-(1'-propenyl)-17β-3'-oxidoestra-4-en-3-one

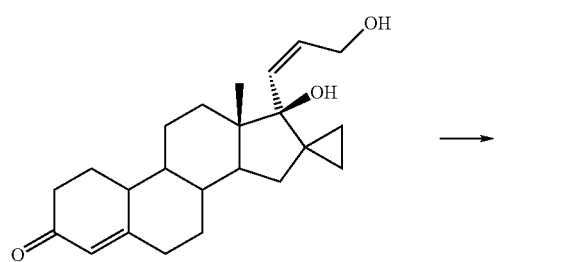

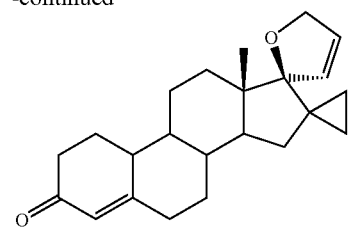

Similarly to Example 1, 400 mg of the compound prepared according to Example 6a is reacted, and after processing and purification, 236 mg of the title compound is isolated.

$^1$H-NMR (CDCl$_3$): δ=0.20 (1H), 0.34 (1H), 0.44 (1H), 0.84-1.06 (2H), 1.11 (3H), 1.12 (1H), 1.23-1.72 (8H), 1.79-1.92 (2H), 2.14 (1H), 2.24-2.38 (3H), 2.41-2.57 (2H), 4.37 (1H), 4.50 (1H), 5.76 (1H), 5.86 (1H), 5.87 (1H) ppm.

Example 6a 16,16-(1,2-Ethanediyl)-17α(Z)-(3'-hydroxypropen-1'-yl)-17β-hydroxyestra-4-en-3-one

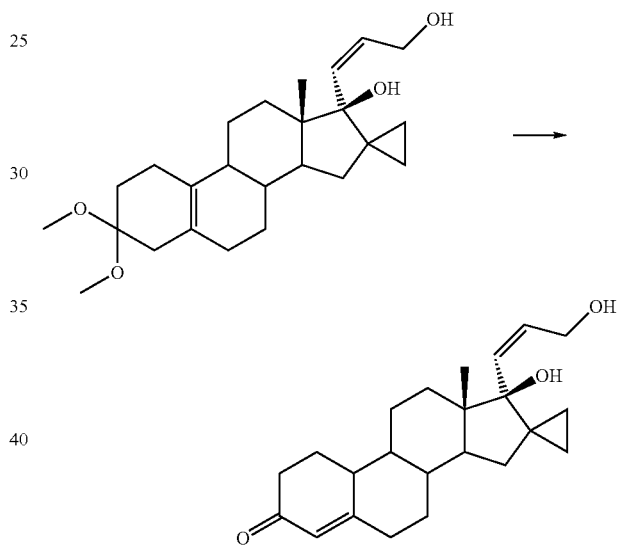

2.83 g of the compound prepared according to Example 6b is reacted as in Example 1a and, after processing and purification, 1.64 g of the title compound is isolated.

Example 6b 3,3-Dimethoxy-16,16-(1,2-ethanediyl)-17α(Z)-(3'-hydroxypropen-1'-yl)-17β-hydroxyestra-5(10)-ene

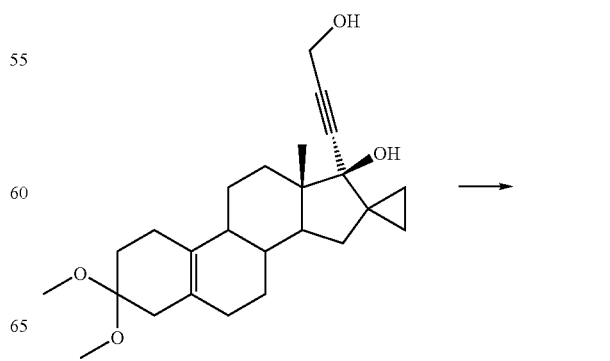

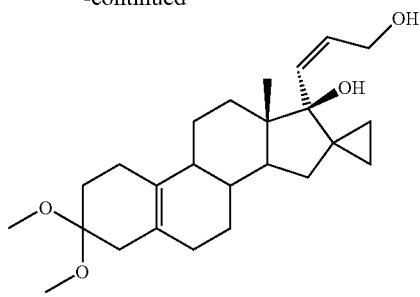

2.98 g of the compound prepared according to Example 6c is reacted as in Example 1b and, after processing, 2.84 g of the title compound is isolated, and the title compound is reacted further without purification.

Example 6c 3,3-Dimethoxy-16,16-(1,2-ethanediyl)-17α(Z)-(3'-hydroxypropyn-1'-yl)-17β-hydroxyestra-5(10)-ene

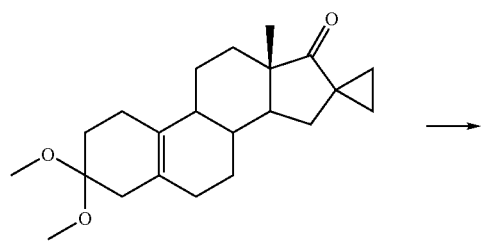

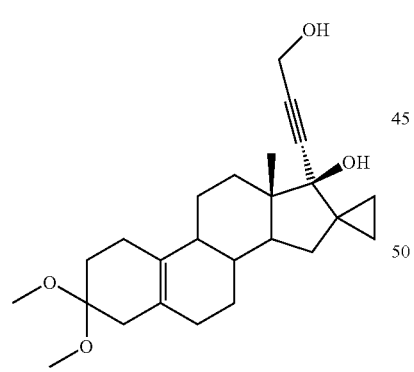

100 mg of the compound prepared according to Example 6d is reacted as in Example 1c and, after processing and purification, 116 mg of the title compound is isolated, and the title compound is reacted further without purification.

Example 6d 16,16-cyclopropanation from 16,16-methylene 3,3-pimethoxy-16,16-(1,2-ethanediyl)-estra-5(10)-en-17-one

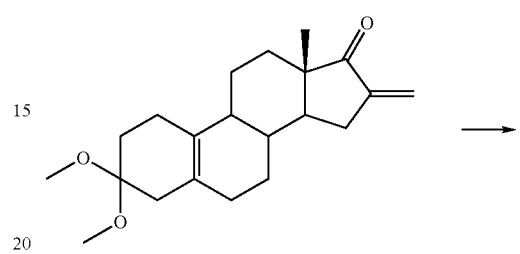

1.05 g of a 60% suspension of sodium hydride in white oil is added in portions, at 23° C., to a solution of 5.61 g sulfoxonium iodide in 100 ml dimethylsulfoxide. It is stirred for a further 2 hours, then a solution of 2.1 g of the compound prepared according to Example 6e in 40 ml dimethylsulfoxide is added dropwise and left to react for a further 16 hours. It is poured into water, extracted with ethyl acetate several times, the combined organic extracts are washed with saturated sodium chloride solution and dried over sodium sulfate. 2.52 g of the title compound is isolated, which still contains residual amounts of white oil, and the title compound is reacted further without additional purification.

Example 6e 16,16-methylene from silylenol ether 3,3-Dimethoxy-16-methylene-estra-5(10)-en-17-one

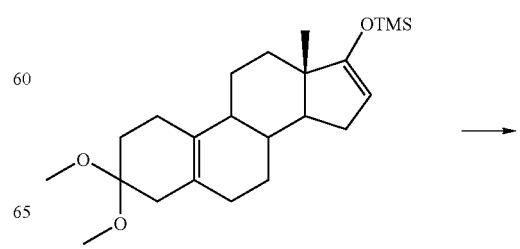

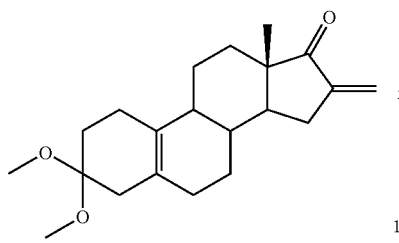

10 ml of N,N,N',N'-tetramethyldiamonomethane is added to a solution of 6.1 g 3,3-dimethoxy-17-trimethylsilyloxy-estra-5(10)16-diene in 30 ml tetrahydrofuran, it is cooled to 3° C. and 10 ml acetic acid anhydride is added. It is allowed to warm up to 23° C. and is left to react for 2 days. It is poured into saturated sodium hydrogencarbonate solution, extracted with ethyl acetate several times, the combined organic extracts are washed with saturated sodium chloride solution and dried over sodium sulfate. It is purified by silica gel chromatography, and 1.6 g of the title compound is isolated.

Example 7

18-Methyl-17α-(1'-propenyl)-17β-3'-oxidoestra-4-en-3-one

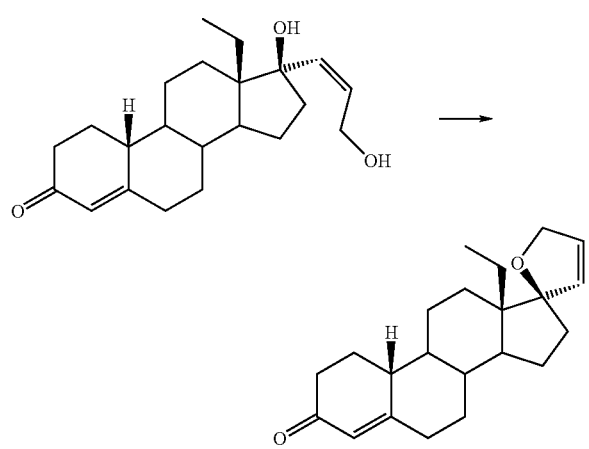

Similarly to Example 1, 10 g of the compound prepared according to Example 7a is reacted and, after processing and purification, 8.26 g of the title compound is isolated.

$^1$H-NMR (CDCl$_3$): δ=0.79 (1H), 0.91-1.11 (3H), 1.00 (3H), 1.20 (1H), 1.37 (1H), 1.45-1.65 (5H), 1.73-1.82 (3H), 1.86 (1H), 2.04-2.13 (2H), 2.21-2.32 (3H), 2.40 (1H), 2.48 (1H), 4.49 (1H), 4.57 (1H), 5.77 (1H), 5.82 (1H), 5.83 (1H) ppm.

Example 7a

17α(Z)-(3'-Hydroxypropen-1'-yl)-18-methyl-17β-hydroxyestra-4-en-3-one

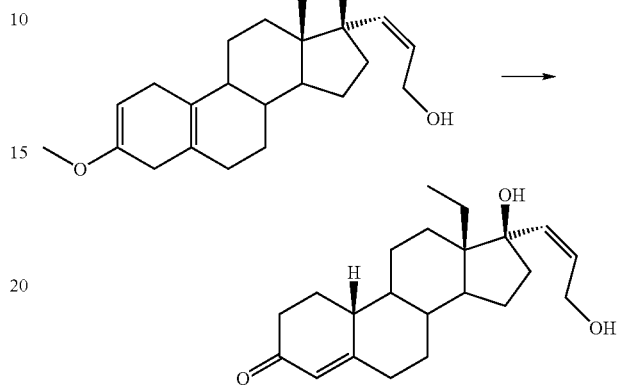

6.35 g of the compound prepared according to Example 7b is reacted as in Example 1a and, after processing and purification, 3.02 g of the title compound is isolated.

Example 7b

17α(Z)-(3'-Hydroxypropen-1'-yl)-3-methoxy-18-methyl-17β-hydroxyestra-2,5(10)-diene

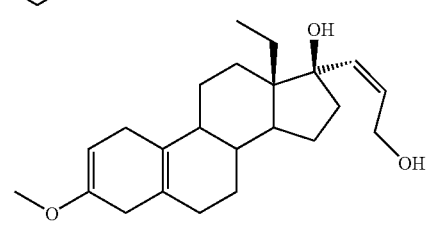

7.86 g of the compound prepared according to Example 7c is reacted as in Example 1b and, after processing, 6.35 g of the title compound is isolated, and the title compound is reacted further without purification.

Example 7c

17α(Z)-(3'-Hydroxypropyn-1'-yl)-3-methoxy-18-methyl-17β-hydroxyestra-2,5(10)-diene

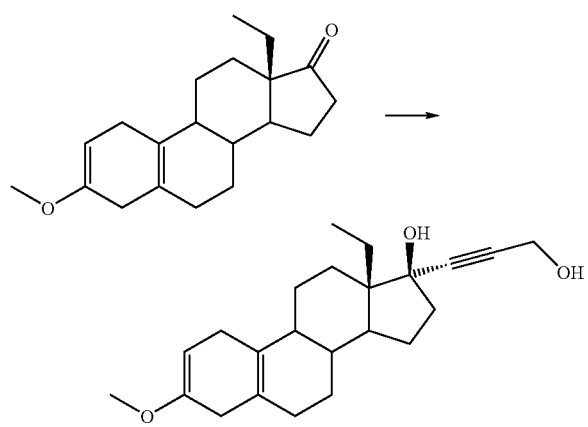

5.0 g of 3-methoxy-18-methyl-17β-hydroxyestra-2,5(10)-dien-17-one is reacted as in Example 1c and, after processing, 7.86 g of the title compound is isolated, and the title compound is reacted further without purification.

Example 8

18-Methyl-17α-(1'-propenyl)-17β-3'-oxidoestra-4,6-dien-3-one

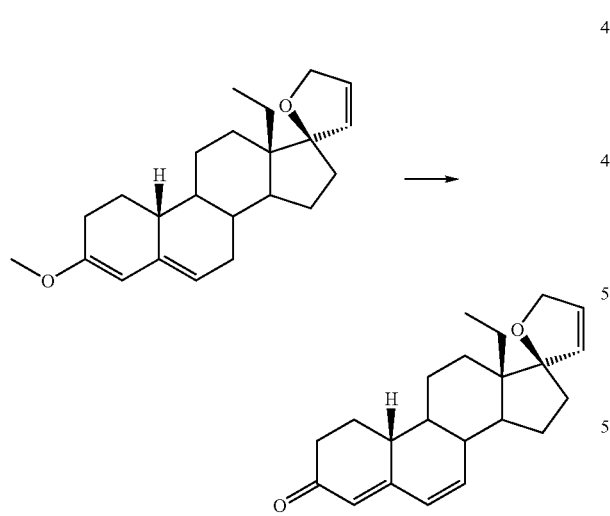

Similarly to Example 2, 1.04 g of the compound prepared according to Example 8a is reacted and, after processing and purification, 498 mg of the title compound is isolated.

$^1$H-NMR (CDCl$_3$): δ=0.93-1.16 (3H), 1.01 (3H), 1.30-1.65 (5H), 1.72-1.88 (4H), 2.12 (1H), 2.22-2.41 (4H), 2.54 (1H), 4.50 (1H), 4.58 (1H), 5.76 (1H), 5.77 (1H), 5.85 (1H), 6.20 (2H) ppm.

Example 8a

3-Methoxy-18-methyl-17α-(1'-propenyl)-17β-3'-oxidoestra-3,5-diene

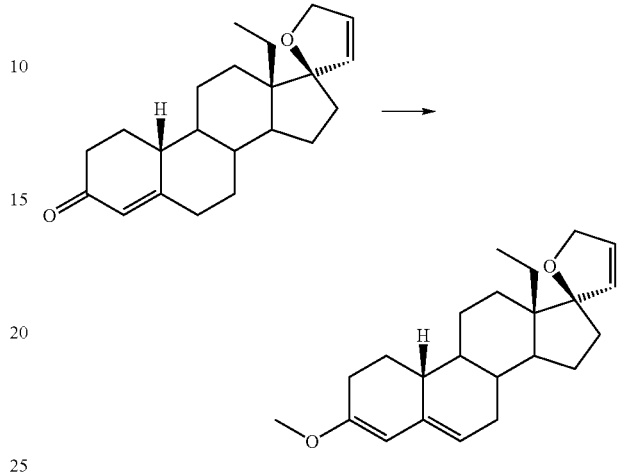

Similarly to Example 2a, 10 g of the compound prepared according to Example 1 is reacted and, after processing, 11 g of the title compound is isolated, and the title compound is reacted further without purification.

Example 9

7α,18-Dimethyl-17α-(1'-propenyl)-17β-3'-oxidoestra-4-en-3-one (A) and 7β,18-dimethyl-17α-(1'-propenyl)-17β-3'-oxidoestra-4-en-3-one (B)

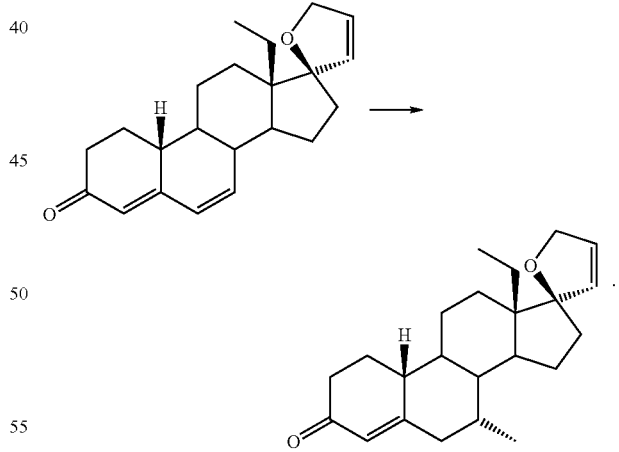

Similarly to Example 3, 200 mg of the compound prepared according to Example 8 is reacted and, after processing and purification, 82 mg of the title compound A is isolated along with a still contaminated mixture that contains proportions of the title compound B.

$^1$H-NMR (CDCl$_3$) of A: δ=0.78 (3H), 0.92 (1H), 0.98-1.08 (2H), 1.00 (3H), 1.27-1.39 (2H), 1.49-1.60 (4H), 1.69 (1H), 1.73 (1H), 1.77-1.85 (2H), 1.97-2.05 (2H), 2.09 (1H), 2.22-2.30 (3H), 2.40 (1H), 2.48 (1H), 4.50 (1H), 4.57 (1H), 5.79 (1H), 5.83 (1H), 5.84 (1H) ppm.

Example 10

7α-Ethyl-18-methyl-17α-(1'-propenyl)-17β-3'-oxidoestra-4-en-3-one (A) and 7β-ethyl-18-methyl-17α-(1'-propenyl)-17β-3'-oxidoestra-4-en-3-one (B)

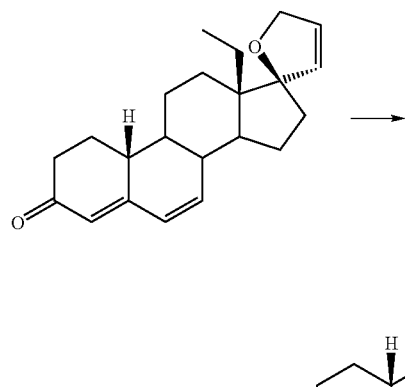

Similarly to Example 3, using ethylmagnesium chloride, 200 mg of the compound prepared according to Example 8 is reacted and, after processing and purification, 28 mg of the title compound A is isolated along with a still contaminated mixture, which still contains small proportions of the title compound B.

$^1$H-NMR (CDCl$_3$) of A: δ=0.87 (3H), 0.88-1.06 (2H), 1.00 (3H), 1.29-1.44 (3H), 1.48-1.56(4H), 1.64 (1H), 1.69-1.85 (4H), 2.03 (1H), 2.08 (1H), 2.23-2.31 (3H), 2.40 (1H), 2.56 (1H), 4.49 (1H), 4.57 (1H), 5.79 (1H), 5.84 (2H) ppm.

Example 11

7α-Vinyl-18-methyl-17α-(1'-propenyl)-17β-3'-oxidoestra-4-en-3-one (A) and 7β-vinyl-18-methyl-17α-(1'-propenyl)-17β-3'-oxidoestra-4-en-3-one (B)

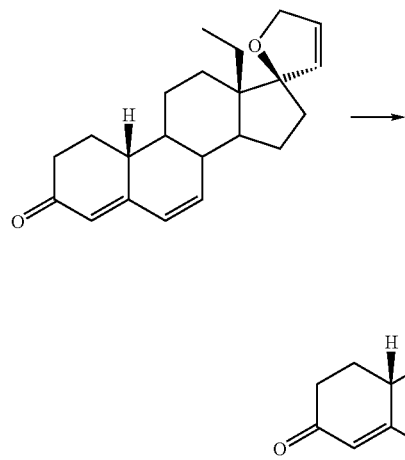

Similarly to Example 3, using vinylmagnesium chloride, 200 mg of the compound prepared according to Example 8 is reacted and, after processing and purification, 41 mg of the title compound A is isolated along with a still contaminated mixture that contains proportions of the title compound B.

$^1$H-NMR (CD$_2$Cl$_2$) of A: δ=0.88-1.18 (3H), 1.02 (3H), 1.24-1.45 (2H), 1.50-1.90 (8H), 2.07 (1H), 2.14 (1H), 2.25-2.66 (6H), 4.45-4.58 (2H), 5.07-5.18 (2H), 5.74-5.89 (4H) ppm.

Example 12

7α-Cyclopropyl-18-methyl-17α-(1'-propenyl)-17β-3'-oxidoestra-4-en-3-one (A) and 7β-cyclopropyl-18-methyl-17α-(1'-propenyl)-17β-3'-oxidoestra-4-en-3-one (B)

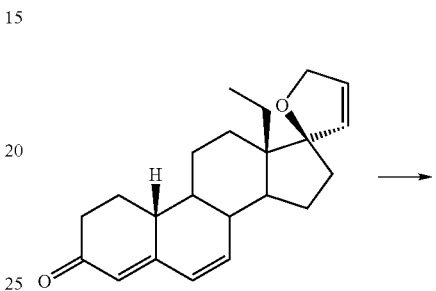

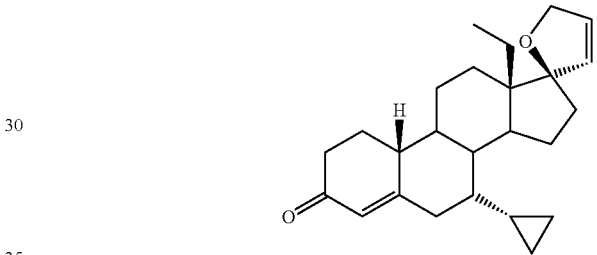

Similarly to Example 3, 200 mg of the compound prepared according to Example 8 using cyclopropylmagnesium bromide is reacted and, after processing and purification, 47 mg of the title compound A is isolated along with a still contaminated mixture that contains proportions of the title compound B.

$^1$H-NMR (CD$_2$Cl$_2$) of A: δ=−0.02 (1H), 0.35 (1H), 0.46 (1H), 0.51-0.65 (2H), 0.94-1.19 (3H), 1.02 (3H), 1.28-1.41 (2H), 1.51-1.94 (10H), 2.07 (1H), 2.14 (1H), 2.26-2.56 (4H), 4.50 (1H), 4.57 (1H), 5.81-5.92 (3H) ppm.

Example 13

Introduction of 6-hydroxymethyl

6β-Hydroxymethylene-18-methyl-17α-(1'-propenyl)-17β-3'-oxidoestra-4-en-3-one

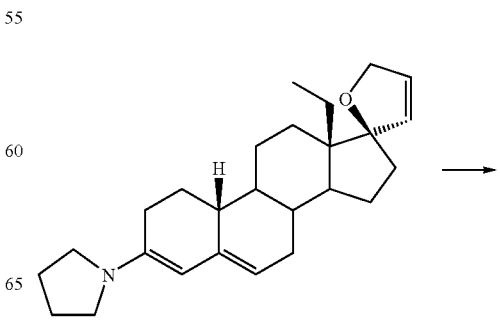

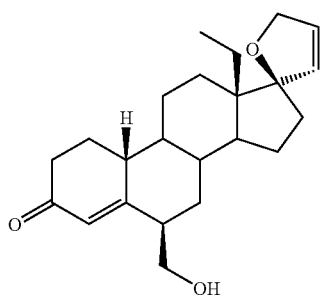

860 µl of 37% aqueous formaldehyde solution is added to a solution of 830 mg of the compound prepared according to Example 13a in a mixture of 8 ml toluene and 18 ml ethanol and it is stirred for 6 hours at 23° C. It is concentrated by evaporation and the residue is purified by chromatography. 260 mg of the title compound is isolated.

$^1$H-NMR (CD$_2$Cl$_2$): δ=0.78 (1H), 0.88-1.66 (11H), 0.97 (3H), 1.69-1.81 (3H), 1.86 (1H), 2.04 (1H), 2.11-2.41 (4H), 2.60 (1H), 3.65 (2H), 4.44 (1H), 4.51 (1H), 5.76-5.86 (3H) ppm.

Example 13a

Dienamine Formation

18-Methyl-3-pyrrolidinyl-17α-(1'-propenyl)-17β-3'-oxidoestra-3,5-diene

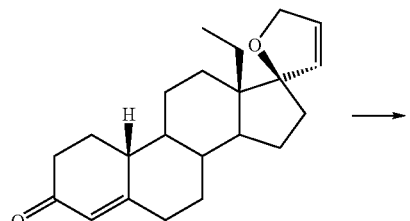

584 µl pyrrolidine is added to a solution of 1.0 g of the compound prepared according to Example 7 in 10 ml methanol and it is heated under reflux for 2 hours. It is cooled, the precipitate is filtered off with suction, it is washed with a little cold methanol and 840 mg of the title compound is obtained, and the title compound is reacted further without additional purification.

Example 14

6β,7β-Methylene-17α-(1'-propenyl)-17β-3'-oxidoestra-4-en-3-one (A) and 6α,7α-methylene-17α-(1'-propenyl)-17β-3'-oxidoestra-4-en-3-one (B)

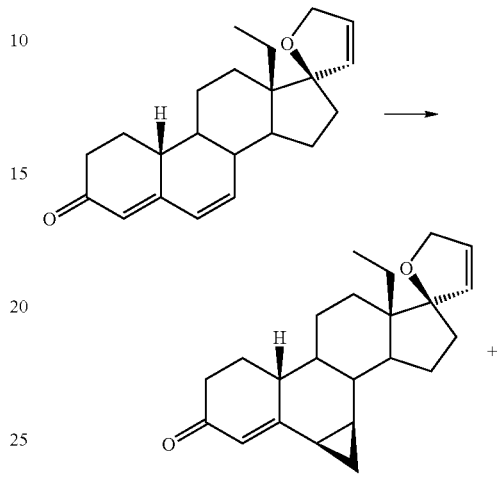

215 mg trimethylsulfoxonium iodide is dissolved in 4.1 ml dimethylsulfoxide, 38.9 mg of a 60% sodium hydride dispersion is added and it is stirred for 1.25 hours at 23° C. Then a solution of 76 mg of the compound prepared according to Example 8 in 1.66 ml dimethylsulfoxide is added dropwise and it is stirred for a further 5 hours at 23° C. It is poured into water, extracted with ethyl acetate several times, the combined organic extracts are washed with water and saturated sodium chloride solution and dried over sodium sulfate. The residue obtained after filtration and removal of the solvent is purified by chromatography. 8.2 mg of a mixture of the title compounds A and B is isolated.

Example 15

7α-Cyclopropyl-17α-(1'-propenyl)-17β-3'-oxidoestra-4-en-3-one (A) and 7β-cyclopropyl-17α-(1'-propenyl)-17β-3'-oxidoestra-4-en-3-one (B)

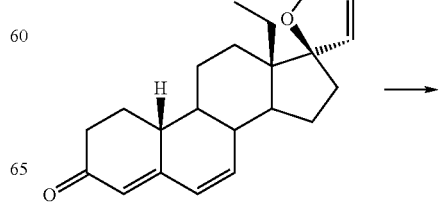

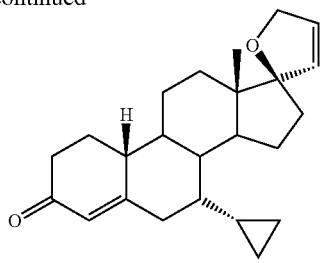

Similarly to Example 3, 200 mg of the compound prepared according to Example 2 using cyclopropylmagnesium bromide is reacted and, after processing and purification, 13.3 mg of the title compound A is isolated along with a still contaminated mixture that contains proportions of the title compound B.

$^1$H-NMR (CDCl$_2$): δ=−0.06 (1H), 0.32 (1H), 0.41 (1H), 0.46-0.60 (2H), 0.93 (3H), 1.05-1.99 (13H), 2.09 (1H), 2.20-2.51 (5H), 4.51 (2H), 5.31 (1H), 5.80 (1H), 8.53 (1H) ppm.

Example 16

6,6-cyclopropanation (6,6-1,2-Ethanediyl)-17α-(1'-propenyl)-17β-3'-oxidoestra-4-en-3-one

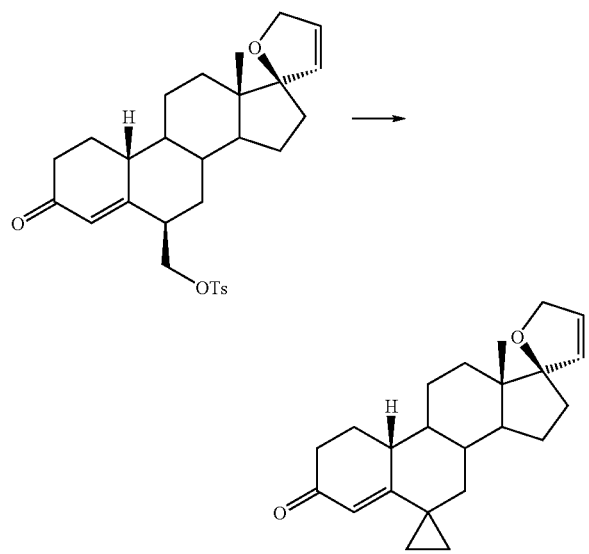

64 mg trimethylsulfoxonium iodide is dissolved in 1.2'ml dimethylsulfoxide, 11.7 mg of a 60% sodium hydride dispersion is added and it is stirred for 2 hours at 23° C. Then a solution of 36 mg of the compound prepared according to Example 16a in 0.46 ml dimethylsulfoxide is added dropwise and it is stirred for a further 2 hours at 23° C. It is poured into water, extracted with ethyl acetate several times, the combined organic extracts are washed with water and saturated sodium chloride solution and dried over sodium sulfate. The residue obtained after filtration and removal of the solvent is purified by chromatography. 4.2 mg of the title compound is isolated.

$^1$H-NMR (CD$_2$Cl$_2$): δ=0.42 (1H), 0.56 (1H), 0.74 (1H), 0.93 (1H), 0.99 (3H), 1.04 (1H), 1.17-1.79 (11H), 1.88 (1H), 2.01 (1H), 2.18-2.41 (4H), 4.54 (2H), 5.66 (1H), 5.86 (2H) ppm.

Example 16a

Formation of 6-tosyloxymethyl

17α-(1'-Propenyl)-6β-(p-tolylsulfonyloxymethyl)-17β-3'-oxidoestra-4-en-3-one

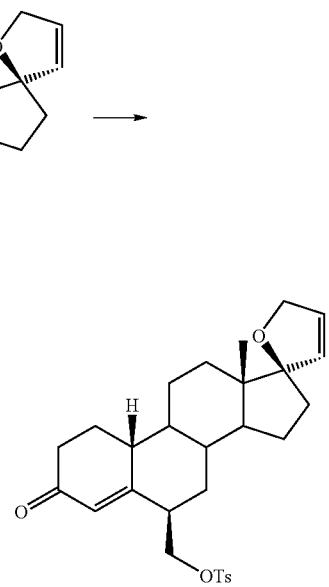

1.3 ml triethylamine and 456 mg p-toluenesulfonic acid chloride are added to a solution of 328 mg of the compound prepared according to Example 16b in 13 ml dichloromethane and it is stirred for 60 hours at 0° C. It is poured into saturated sodium carbonate solution, extracted with ethyl acetate several times, the combined organic extracts are washed with water and saturated sodium chloride solution and dried over sodium sulfate. The residue obtained after filtration and removal of the solvent is purified by chromatography. 81 mg of the title compound is isolated.

Example 16b

6β-(Hydroxymethylene)-17α-(1-propenyl)-17β-3'-oxidoestra-4-en-3-one

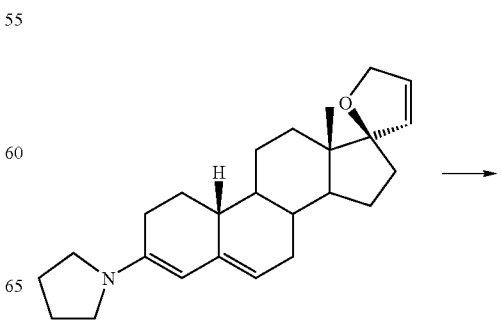

-continued

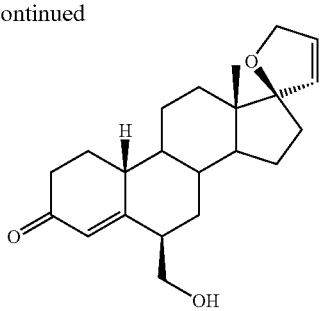

Similarly to Example 13, 350 mg of the compound prepared according to Example 16c is reacted and the raw product is reacted further after processing without purification.

Example 16c

3-Pyrrolidinyl-17α-(1'-propenyl)-17β-3'-oxidoestra-3,5-diene

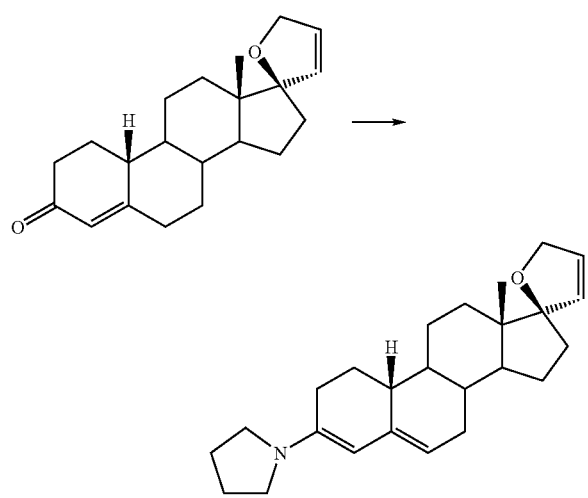

Similarly to Example 13a, 745 mg of the compound prepared according to Example 1 is reacted and, after processing, 356 mg of the title compound is isolated.

Example 17

Inert depot systems amenable to intrauterine implantation and composed of a biodegradable polymer or a synthetic silicone polymer consisting of an active ingredient-containing core in the appropriate polymer-active ingredient mixing ratio, surrounded by a polymer membrane ensuring the desired daily release rate, are introduced into the lumen of the rat uterus. The female animals are castrated beforehand and pretreated with estradiol for three days. The implants of different length (5-20 mm) and a restricted diameter (1.1 to 2 mm) remain for between 4 and 14 days in the rat uterus in order to investigate the local and systemic progestational effect of the released active ingredient on the basis of various parameters in different tissues. The following parameters are measured: 1) local progestational effect on the uterus on the basis of the weight of the uterus, the histologically detectable epithelial height and the expression of progestogen-regulated marker genes (e.g. IGFBP-1); 2) systemic progestational effect on the mammary gland on the basis of the expression of progestogen-regulated marker genes (e.g. RankL), 3) systemic progestational effect on the pituitary on the basis of the LH level (reduction in the estrogen-induced elevation of the LH level).

The compounds of the present invention show a significant progestational effect in the uterus which is comparable to a corresponding treatment with a levonorgestrel-containing depot system such as MIRENA®.

TABLE 1

Receptor binding values

| Ex. | Structure | Receptor binding | | | | | |
|---|---|---|---|---|---|---|---|
| | | Progesterone receptor (PR) | | Mineralocorticoid receptor (MR) | Androgen receptor | | CF PR/ CF MR |
| | | IC50 [nM] | Competition factor | Competition factor | IC50 [nM] | Competition factor | |
| A | Chiral | 43.3 | 2.7 | 0.5 | 630 | 37 | 5.40 |

TABLE 1-continued

Receptor binding values

| Ex. | Structure | Receptor binding | | | | | CF PR/ CF MR |
|---|---|---|---|---|---|---|---|
| | | Progesterone receptor (PR) | | Mineralocorticoid receptor (MR) | Androgen receptor | | |
| | | IC50 [nM] | Competition factor | Competition factor | IC50 [nM] | Competition factor | |
| 1 | (structure) | 3 | 0.46 | 2.6 | 27 | 3.3 | 0.18 |
| 2 | (structure) | 55.5 | 2.29 | 8.9 | 660 | 28.7 | 0.26 |
| 3 | (structure) | 62 | 2.41 | 3.2 | 45 | 2.0 | 0.75 |
| 4 | (structure) | 130 | 11.75 | 4.1 | 64 | 2.9 | 2.87 |
| 5 | (structure) | | 2.46 | 2.6 | 53 | 2.2 | 0.95 |

TABLE 1-continued

| | | Receptor binding values | | | | | |
|---|---|---|---|---|---|---|---|
| | | Receptor binding | | | | | |
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| 6 | (structure) | 110 | 3.41 | 22.9 | 140 | 15.7 | 0.15 |
| 7 | (structure) | 5.3 | 0.19 | 1.6 | 0 | 0.5 | 0.12 |
| 8 | (structure) | 1.78 | | 1.2 | 1200 | 47.9 | 1.48 |
| 9 | (structure) | 77 | 3.26 | 1.6 | 81 | 3.0 | 2.04 |
| 10 | (structure) | 170 | 7.03 | 1.1 | 110 | 4.1 | 6.39 |

TABLE 1-continued
Receptor binding values
| | | Receptor binding | | | | | |
|---|---|---|---|---|---|---|---|
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| 11 | 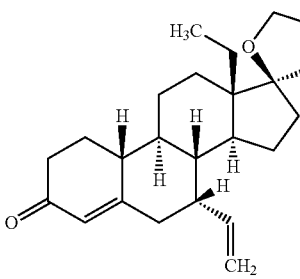 | 170 | 6.24 | 1.3 | 1300 | 4.7 | 4.80 |
| 12 | 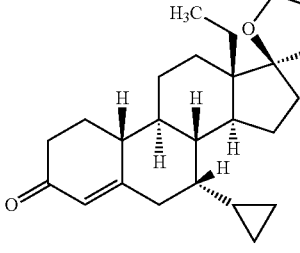 | 210 | 8.51 | 2.0 | 190 | 6.0 | 4.26 |
| 13 | 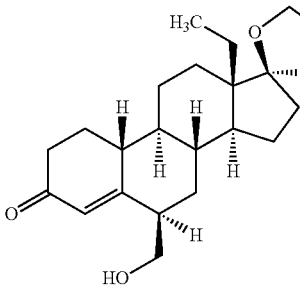 | 2100 | 88.59 | 2.2 | 1000 | 1000.0 | 40.27 |

TABLE 2

| | | Values for in vitro transactivation | | | | | | | |
|---|---|---|---|---|---|---|---|---|---|
| | | In vitro transactivation | | | | | | | |
| | | Progesterone receptor | | Mineralocorticoid receptor | | Androgen receptor | | | |
| Ex. | Structure | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| A | *Chiral structure* | 88 | 72.2 | 3.3 | 64.1 | 112.5 | 24.26 | 27 | 54.58 |
| 1 | *Chiral structure* | | | 31 | 83.0 | 4.8 | 62.7 | 26 | 29 |
| 2 | *Chiral structure* | 2.9 | 36.4 | 92 | 135.6 | 110 | 31.88 | 130 | 34.38 |
| 3 | *Chiral structure* | 3.7 | 61.6 | 17 | 112.2 | 2.3 | 80.21 | 1000 | 5 |
| 4 | *Chiral structure* | 67.0 | 65.1 | 310 | 82.2 | 7.3 | 62.32 | 1000 | 5 |

TABLE 2-continued

Values for in vitro transactivation

| Ex. | Structure | In vitro transactivation |||||||
|---|---|---|---|---|---|---|---|---|
| | | Progesterone receptor || Mineralocorticoid receptor || Androgen receptor ||||
| | | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| 5 | | 1.2 | 21.9 | 57 | 120.6 | 3.7 | 86.78 | 1000 | 5 |
| 6 | | | | 1000 | 65.1 | 6.7 | 49.7 | 11 | 70.11 |
| 7 | | | | 5 | 87.8 | 3.7 | 78.3 | 160 | 25.4 |
| 8 | | 1.1 | 12.3 | 66 | 111.7 | 55 | 62.02 | 1000 | 5 |
| 9 | | 7.1 | 55.9 | 38 | 104.9 | 3 | 77.9 | 1000 | 5 |

TABLE 2-continued

Values for in vitro transactivation

| Ex. | Structure | | Progesterone receptor | | Mineralocorticoid receptor | | Androgen receptor | | | |
|---|---|---|---|---|---|---|---|---|---|---|
| | | | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| 10 | (structure) Chiral | | 780.0 | 26.4 | 850 | 39.2 | 9.4 | 70.4 | 1000 | 5 |
| 11 | (structure) Chiral | | 100.0 | 29.5 | Partial agonist | | 5.3 | 88.82 | 1000 | 5 |
| 12 | (structure) Chiral | | 55.0 | 30.9 | Partial agonist | | 16 | 70.12 | 1000 | 5 |
| 13 | (structure) Chiral | | 1000.0 | 5.0 | 110 | 98.8 | 1000 | 5 | 140 | 48.11 |

The invention claimed is:
1. The 17-(1'-Propenyl)-17-3'-oxidoestra-4-en-3-one derivative selected from the group comprising of:
   7α-Methyl-17α-(1'-propenyl)-17β-3'-oxidoestra-4-en-3-one;
   7β-Methyl-17α-(1'-propenyl)-17β-3'-oxidoestra-4-en-3-one;
   7α-Ethyl-17α-(1'-propenyl)-17β-3'-oxidoestra-4-en-3-one;
   7β-Ethyl-17α-(1'-propenyl)-17β-3'-oxidoestra-4-en-3-one;
   7α-Vinyl-17α-(1'-propenyl)-17β-3'-oxidoestra-4-en-3-one;

7β-Vinyl-17α-(1'-propenyl)-17β-3'-oxidoestra-4-en-3-one;
7α-Cyclopropyl-17α-(1'-propenyl)-17β-3'-oxidoestra-4-en-3-one;
7β-Cyclopropyl-17α-(1-propenyl)-17β-3'-oxidoestra-4-en-3-one;
6-Methylene-17α-(1'-propenyl)-17β-3'-oxidoestra-4-en-3-one;
6α-Hydroxymethylene-17α-(1'-propenyl)-17β-3'-oxidoestra-4-en-3-one;
6β-Hydroxymethylene-17α-(1'-propenyl)-17β-3'-oxidoestra-4-en-3-one;
6,6-(1,2-Ethanediyl)-17α-(1'-propenyl)-17β-3'-oxidoestra-4-en-3-one;
6α,7α-Methylene-17α-(1'-propenyl)-17β-3'-oxidoestra-4-en-3-one;
6β,7β-Methylene-17α-(1'-propenyl)-17β-3'-oxidoestra-4-en-3-one;
17α-(1'-Propenyl)-17β-3'-oxidoestra-4,6-dien-3-one;
16,16-(1,2-Ethanediyl)-17α-(1'-propenyl)-17β-3'-oxidoestra-4-en-3-one;
(E/Z)-3-(Hydroxyimino)-7α-methyl-17α-(1'-propenyl)-17β-3'-oxidoestra-4-ene;
(E/Z)-3-(Hydroxyimino)-7β-methyl-17α-(1'-propenyl)-17β-3'-oxidoestra-4-ene;
(E/Z)-3-(Hydroxyimino)-7α-ethyl-17α-(1'-propenyl)-17β-3'-oxidoestra-4-ene;
(E/Z)-3-(Hydroxyimino)-7β-ethyl-17α-(1'-propenyl)-17β-3'-oxidoestra-4-ene;
(E/Z)-3-(Hydroxyimino)-7α-vinyl-17α-(1'-propenyl)-17β-3'-oxidoestra-4-ene;
(E/Z)-3-(Hydroxyimino)-7β-vinyl-17α-(1'-propenyl)-17β-3'-oxidoestra-4-ene;
(E/Z)-3-(Hydroxyimino)-7α-cyclopropyl-17α-(1'-propenyl)-17β-3'-oxidoestra-4-ene;
(E/Z)-3-(Hydroxyimino)-7β-cyclopropyl-17α-(1'-propenyl)-17β-3'-oxidoestra-4-ene;
(E/Z)-3-(Hydroxyimino)-6-methylene-17α-(1'-propenyl)-17β-3'-oxidoestra-4-ene;
(E/Z)-3-(Hydroxyimino)-6α-hydroxymethylene-17α-(1'-propenyl)-17β-3'-oxidoestra-4-ene;
(E/Z)-3-(Hydroxyimino)-6β-hydroxymethylene-17α-(1'-propenyl)-17β-3'-oxidoestra-4-ene;
(E/Z)-3-(Hydroxyimino)-6,6-(1,2-ethanediyl)-17α-(1'-propenyl)-17β-3'-oxidoestra-4-ene;
(E/Z)-3-(Hydroxyimino)-6α,7α-methylene-17α-(1'-propenyl)-17β-3'-oxidoestra-4-ene;
(E/Z)-3-(Hydroxyimino)-6β,7β-methylene-17α-(1'-propenyl)-17β-3'-oxidoestra-4-ene;
(E/Z)-3-(Hydroxyimino)-17α-(1'-propenyl)-17β-3'-oxidoestra-4,6-diene;
(E/Z)-3-(Hydroxyimino)-16,16-(1,2-ethanediyl)-17α-(1'-propenyl)-17β-3'-oxidoestra-4-ene;
7α,18-Dimethyl-17α-(1'-propenyl)-17β-3'-oxidoestra-4-en-3-one;
7β,18-Dimethyl-17α-(1'-propenyl)-17β-3'-oxidoestra-4-en-3-one;
7β-Ethyl-18-methyl-17α-(1'-propenyl)-17β-3'-oxidoestra-4-en-3-one;
7α-Vinyl-18-methyl-17α-(1'-propenyl)-17β-3'-oxidoestra-4-en-3-one;
7β-Vinyl-18-methyl-17α-(1'-propenyl)-17β-3'-oxidoestra-4-en-3-one;
7α-Cyclopropyl-18-methyl-17α-(1'-propenyl)-17β-3'-oxidoestra-4-en-3-one;
7β-Cyclopropyl-18-methyl-17α-(1'-propenyl)-17β-3'-oxidoestra-4-en-3-one;
6-Methylene-17α-(1'-propenyl)-18-methyl-17β-3'-oxidoestra-4-en-3-one;
6α-Hydroxymethylene-17α-(1'-propenyl)-18-methyl-17β-3'-oxidoestra-4-en-3-one;
6,6-(1,2-Ethanediyl)-17α-(1'-propenyl)-18-methyl-17β-3'-oxidoestra-4-en-3-one;
6α,7α-Methylene-17α-(1'-propenyl)-18-methyl-17β-3'-oxidoestra-4-en-3-one;
6β,7β-Methylene-17α-(1'-propenyl)-18-methyl-17β-3'-oxidoestra-4-en-3-one;
17α-(1'-Propenyl)-18-methyl-17β-3'-oxidoestra-4,6-dien-3-one;
16,16-(1,2-Ethanediyl)-17α-(1'-propenyl)-18-methyl-17β-3'-oxidoestra-4-en-3-one;
(E/Z)-3-(Hydroxyimino)-18-methyl-17α-(1'-propenyl)-17β-3'-oxidoestra-4-ene;
(E/Z)-3-(Hydroxyimino)-7α,18-dimethyl-17α-(1'-propenyl)-17β-3'-oxidoestra-4-ene;
(E/Z)-3-(Hydroxyimino)-7β,18-dimethyl-17α-(1'-propenyl)-17β-3'-oxidoestra-4-ene;
(E/Z)-3-(Hydroxyimino)-7α-ethyl-18-methyl-17α-(1'-propenyl)-17β-3'-oxidoestra-4-ene;
(E/Z)-3-(Hydroxyimino)-7β-ethyl-18-methyl-17α-(1'-propenyl)-17β-3'-oxidoestra-4-ene;
(E/Z)-3-(Hydroxyimino)-7α-vinyl-18-methyl-17α-(1'-propenyl)-17β-3'-oxidoestra-4-ene;
(E/Z)-3-(Hydroxyimino)-7β-vinyl-18-methyl-17α-(1'-propenyl)-17β-3'-oxidoestra-4-ene;
(E/Z)-3-(Hydroxyimino)-7α-cyclopropyl-18-methyl-17α-(1'-propenyl)-17β-3'-oxidoestra-4-ene;
(E/Z)-3-(Hydroxyimino)-7β-cyclopropyl-18-methyl-17α-(1'-propenyl)-17β-3'-oxidoestra-4-ene;
(E/Z)-3-(Hydroxyimino)-6-methylene-17α-(1'-propenyl)-18-methyl-17β-3'-oxidoestra-4-ene;
(E/Z)-3-(Hydroxyimino)-6α-hydroxymethylene-17α-(1'-propenyl)-18-methyl-17β-3'-oxidoestra-4-ene;
(E/Z)-3-(Hydroxyimino)-6β-hydroxymethylene-17α-(1-propenyl)-18-methyl-17β-3'-oxidoestra-4-ene;
(E/Z)-3-(Hydroxyimino)-6,6-(1,2-ethanediyl)-17α-(1'-propenyl)-18-methyl-17β-3'-oxidoestra-4-ene;
(E/Z)-3-(Hydroxyimino)-6α,7α-methylene-17α-(1'-propenyl)-18-methyl-17β-3'-oxidoestra-4-ene;
(E/Z)-3-(Hydroxyimino)-6β,7β-methylene-17α-(1'-propenyl)-18-methyl-17β-3'-oxidoestra-4-ene;
(E/Z)-3-(Hydroxyimino)-18-methyl-17α-(1'-propenyl)-17β-3'-oxidoestra-4,6-diene; and
(E/Z)-3-(Hydroxyimino)-16,16-(1,2-ethanediyl)-17α-(1'-propenyl)-18-methyl-17β-3'-oxidoestra-4-ene.

2. A medicinal product, containing at least one 17-(1'-propenyl)-17-3'-oxidoestra-4-en-3-one derivative as claimed in claim 1 and at least one suitable pharmaceutically harmless additive.

3. The medicinal product as claimed in claim 2, additionally containing at least one estrogen.

4. The medicinal product as claimed in claim 3, characterized in that the estrogen is ethinylestradiol.

5. The medicinal product as claimed in claim 3, characterized in that the estrogen is estradiol valerate.

6. The medicinal product as claimed in claim 3, characterized in that the estrogen is a natural estrogen.

7. The medicinal product as claimed in claim 6, characterized in that the natural estrogen is estradiol.

8. The medicinal product as claimed in claim 6, characterized in that the natural estrogen is a conjugated estrogen.

9. A method of contraception comprising the step of administering a compound according to claim 1 to a woman in need thereof.

\* \* \* \* \*